(12) United States Patent
Lin et al.

(10) Patent No.: US 11,253,581 B2
(45) Date of Patent: Feb. 22, 2022

(54) COMPOSITION FOR PREVENTING OR TREATING *MYCOPLASMA SYNOVIAE* INFECTION

(71) Applicant: AGRICULTURAL TECHNOLOGY RESEARCH INSTITUTE, HsinChu (TW)

(72) Inventors: Jiunn-Horng Lin, HsinChu (TW); Ho-Yuan Chou, HsinChu (TW); Jyh-Perng Wang, HsinChu (TW); Zeng-Weng Chen, HsinChu (TW); Weng-Zeng Huang, HsinChu (TW); Hsiu-Hui Wu, HsinChu (TW); Hui-Jie Lin, HsinChu (TW); Sheng-Xiang Huang, HsinChu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 136 days.

(21) Appl. No.: 16/755,623

(22) PCT Filed: Nov. 1, 2017

(86) PCT No.: PCT/CN2017/108887
§ 371 (c)(1),
(2) Date: Apr. 13, 2020

(87) PCT Pub. No.: WO2019/084833
PCT Pub. Date: May 9, 2019

(65) Prior Publication Data
US 2021/0322530 A1    Oct. 21, 2021

(51) Int. Cl.
*A61K 39/02* (2006.01)
*A61K 45/06* (2006.01)
*A61K 38/16* (2006.01)
*A61P 31/04* (2006.01)
*A61K 39/00* (2006.01)

(52) U.S. Cl.
CPC ........ *A61K 39/0241* (2013.01); *A61K 38/164* (2013.01); *A61K 45/06* (2013.01); *A61P 31/04* (2018.01); *A61K 2039/552* (2013.01); *A61K 2039/55505* (2013.01); *A61K 2039/55516* (2013.01); *A61K 2039/55566* (2013.01)

(58) Field of Classification Search
None
See application file for complete search history.

(56) References Cited

U.S. PATENT DOCUMENTS 9,951,109 B2    4/2018   Lin et al.
2007/0009545 A1  1/2007   Frey et al.

FOREIGN PATENT DOCUMENTS

| CN | 101217974 A | 7/2008 |
| CN | 104726413 A | 6/2015 |
| WO | WO 2015/074213 A1 | 5/2015 |
| WO | WO 2017/011918 A1 | 1/2017 |

OTHER PUBLICATIONS

International Search Report (PCT/ISA/210) issued in PCT/CN2017/108887, dated Aug. 8, 2018.

*Primary Examiner* — Padmavathi Baskar
(74) *Attorney, Agent, or Firm* — Birch, Stewart, Kolasch & Birch, LLP

(57) ABSTRACT

The present disclosure relates to a composition for preventing and treating *Mycoplasma synoviae* infection, the composition comprising Tuf, NOX, MS53-0285 or a combination thereof as active ingredients. The composition of the present disclosure is effective in alleviating symptoms caused by *Mycoplasma synoviae* infection and can be used as an effective tool in preventing or treating poultry diseases.

18 Claims, 14 Drawing Sheets
Specification includes a Sequence Listing.

COMPOSITION FOR PREVENTING OR TREATING *MYCOPLASMA SYNOVIAE* INFECTION

BACKGROUND

Technical Field

The present application relates to a composition for preventing or treating *Mycoplasma* spp. infection, particularly to a composition for preventing or treating *Mycoplasma synoviae*.

Description of Related Art

*Mycoplasma* spp. is currently known as the smallest prokaryote capable of self-replicating extracellularly. They are spherical with a diameter of 0.3 to 0.9 μm, or filament-like with a length of 1 μm. As fastidious bacteria, they are difficult to culture and their growth rate is very slow. It is known that several types of *Mycoplasma* spp. are associated with a number of human or animal diseases.

Studies have shown that poultry can be infected with dozens of types of *Mycoplasma* spp., including *Mycoplasma synoviae*, a disease-causing microorganism listed in the OIE (World Organization for Animal Health) document regarding *Mycoplasma* diseases. Thus, *Mycoplasma synoviae* is an important pathogen to be taken into consideration for the prevention or treatment in poultry.

*Mycoplasma synoviae* may cause synovitis or arthritis. *Mycoplasma synoviae* infection in broiler chicken will result in lower feed efficiency, higher mortality rate and poultry carcasses condemnation rate. *Mycoplasma synoviae* infection in breeder chickens and layer chickens will result in lower egg production rate and higher embryo mortality rate. *Mycoplasma synoviae* infection in chickens will be more likely to result in secondary infection caused by viral or bacterial pathogens, causing significant financial losses for poultry farmers. Manufacturers of veterinary vaccines worldwide have developed live and inactivated vaccines for the poultry industry; however, culturing *Mycoplasma synoviae* is difficult and costly. Therefore, there remains a need in this field for vaccines that can be used for preventing and treating *Mycoplasma synoviae* infection.

SUMMARY

Accordingly, one object of the present disclosure is to provide antigens suitable for being used in *Mycoplasma synoviae* subunit vaccines, thereby producing subunit vaccines to reduce disease prevention costs.

Another object of the present disclosure is to provide a subunit vaccine with multiple antigens that can be used for preventing and treating *Mycoplasma synoviae* infection. Such vaccine provides better protection than single-antigen vaccines.

To this end, the present disclosure provides a composition for preventing *Mycoplasma synoviae* infection, comprising: active ingredients, which comprise Tuf, NOX, MS53-0285 and a combination thereof, wherein said Tuf has a sequence of SEQ ID NO: 01, said NOX has a sequence of SEQ ID NO: 02, and said MS53-0285 has a sequence of SEQ ID NO: 03; and a pharmaceutically acceptable adjuvant.

Preferably, said active ingredients are at least two proteins selected from the group consisting of: Tuf, NOX and MS53-0285. More preferably, said active ingredients include Tuf, NOX and MS53-0285.

More preferably, said active ingredients have a concentration of 40 to 900 μg/mL based on the total volume of said composition.

Possibly, said pharmaceutically acceptable adjuvant is a complete or incomplete Freund's adjuvant, alumina gel, surfactant, polyanion adjuvant, peptide, oil emulsion, or a combination thereof.

Preferably, said composition further comprises a pharmaceutically acceptable additive. Possibly, said pharmaceutically acceptable additive is a solvent, stabilizer, diluent, preservative, antibacterial agent, antifungal agent, isotonic agent, absorption delaying agent, or a combination thereof.

Preferably, said symptoms caused by *Mycoplasma synoviae* infection are tracheal lesion, air sac lesion, arthritis or a combination thereof.

Preferably, said symptoms caused by *Mycoplasma synoviae* infection are at least arthritis provided that said active ingredients include Tuf. Preferably, said symptoms caused by *Mycoplasma synoviae* infection are at least air sac lesion provided that said active ingredients include NOX and MS53-0285, or a combination thereof. More preferably, said symptoms caused by *Mycoplasma synoviae* infection are at least tracheal lesion provided that said active ingredients include MS53-0285.

Preferably, said symptoms caused by *Mycoplasma synoviae* infection are tracheal lesion, air sac lesion and arthritis provided that said active ingredients comprise Tuf, NOX and MS53-0285.

The present disclosure also provides an expression vector, comprising: a nucleotide sequence of SEQ ID NO: 4, SEQ ID NO: 5, SEQ ID NO: 6 or a combination thereof; expression elements including a promoter and a ribosome binding site; and a fusion partner sequence.

The present disclosure further provides an expression vector, comprising: a nucleotide sequence translated as a protein of Tuf, NOX, MS53-0285 or a combination thereof, wherein said Tuf has a sequence of SEQ ID NO: 01, said NOX has a sequence of SEQ ID NO: 02, and said MS53-0285 has a sequence of SEQ ID NO: 03; expression elements including a promoter and a ribosome binding site; and fusion partner sequences.

Preferably, said fusion partner is DsbC from *E. coli*, MsyB from *E. coli*, FklB from *E. coli* or a combination thereof.

Preferably, said expression vector has a sequence of SEQ ID NO: 07, SEQ ID NO: 08, or SEQ ID NO: 09.

The present disclosure further provides the use of protein for producing a composition for preventing and treating *Mycoplasma synoviae* infection, wherein said protein comprises Tuf, NOX, MS53-0285 or a combination thereof; wherein said Tuf has a sequence of SEQ ID NO: 01, said NOX has a sequence of SEQ ID NO: 02, and said MS53-0285 has a sequence of SEQ ID NO: 03.

In view of the foregoing, the present disclosure discloses antigens used for preventing and treating *Mycoplasma synoviae* infection and as active ingredients for subunit vaccines. The results of the present disclosure not only provide a novel option for preventing *Mycoplasma synoviae* infection, but also discloses that "cocktail" subunit vaccines combining two or more antigens (i.e. containing two or more antigens as active ingredients) have a better immunity-inducing effect.

DETAILED DESCRIPTION

Figure 1:
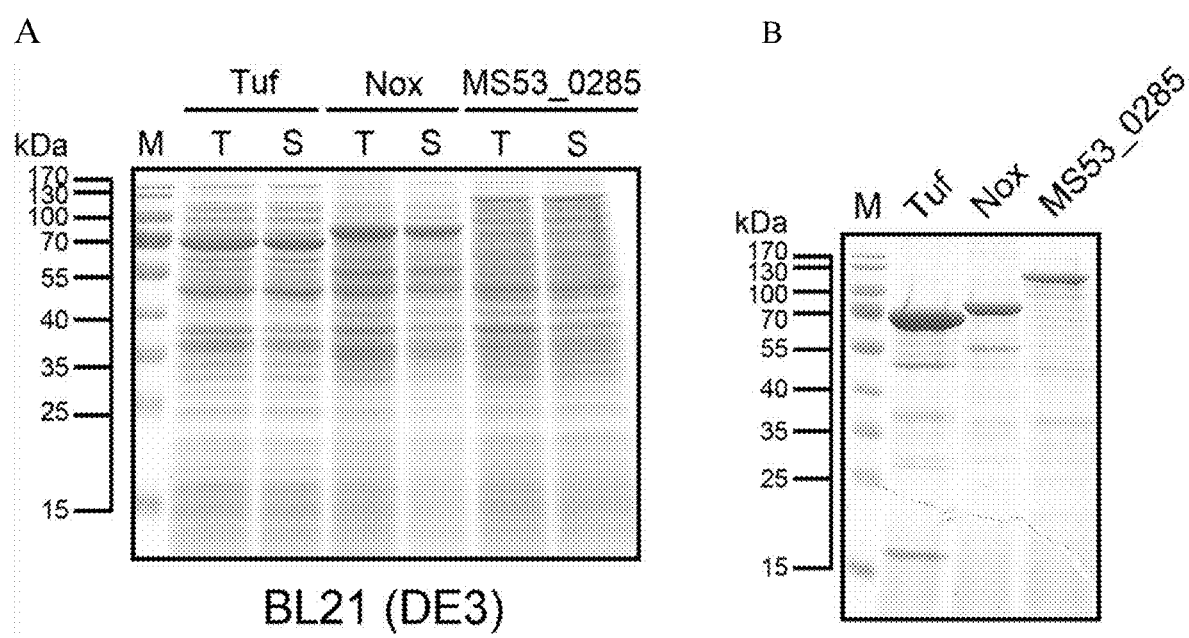
FIG. 1 shows the result of Example 4 of the present invention. (A) Protein electrophoresis was used to evaluate the solubility of the recombinant antigens manufactured in the present disclosure (T represents total cell lysates; S represents soluble fraction). (B) Protein electrophoresis was used to evaluate the purity of the recombinant antigens purified in the present invention.
Figure 2:
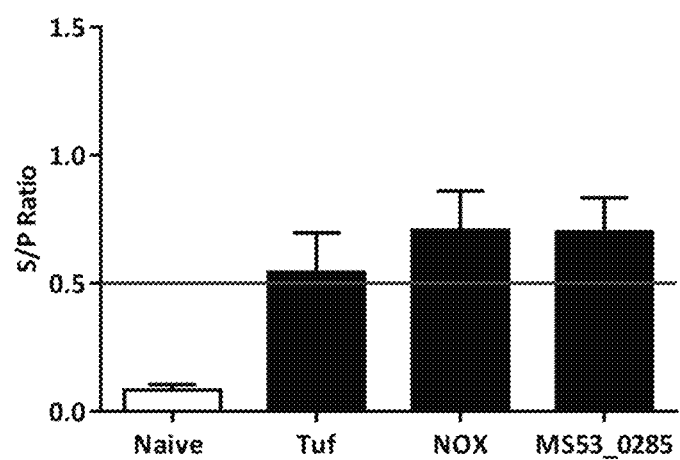
FIG. 2 shows the positive *Mycoplasma synoviae*-specific antibodies responses in the chicken serum of Example 5 of the present invention.

The development results of the present disclosure prove that Tuf, NOX and MS53-0285 can be used as active ingredients in subunit vaccines for preventing and treating *Mycoplasma synoviae* infection. The phrase "preventing and treating *Mycoplasma synoviae* infection" herein refers to reduce infection level of *Mycoplasma synoviae* in poultry, such as alleviating diseases caused by *Mycoplasma synoviae* infection. Said diseases include but not limited to tracheal lesion, air sac lesion or arthritis (such as footpad swelling or footpad inflammation). From a scientific point of view, it is impossible to demonstrate whether the subjects are not infected with said disease-causing microorganisms at all. Therefore, it can be understood by a person having ordinary skill in the art that in the field of disease prevention, the act of "preventing and treating" does not intend to keep the subject from being infected with any of said disease-causing microorganisms.

In one aspect, the present disclosure relates to a composition for preventing and treating *Mycoplasma synoviae* infection. In one preferred embodiment, the composition is a subunit vaccine. In one preferred embodiment, the composition comprises Tuf as active ingredients, and said Tuf has a sequence of SEQ ID NO: 01. In another preferred embodiment, the composition comprises NOX as active ingredients, and said NOX has a sequence of SEQ ID NO: 02. In yet another preferred embodiment, the composition comprises MS53-0285 as an active ingredient, and said MS53-0285 has a sequence of SEQ ID NO: 03.

A person having ordinary skill in the art can readily understand that as long as the antigen determinants on said proteins are not affected, said amino acid sequence can be altered to a certain degree and still falls within the scope of the present invention. For example, a few amino acids in said sequence may be altered by a person having ordinary skill in the art, but the immunity-inducing effect as described herein can still be generated. Alternatively, based on the needs of a person having ordinary skill in the art, other sequences may be added into said sequence to facilitate production without affecting the immunity-inducing effect as described herein. In this regard, the modified sequence should still falls within the scope of the present invention.

In one embodiment, when said active ingredients include Tuf, said symptoms caused by *Mycoplasma synoviae* infection are at least arthritis. Nevertheless, the fact that said active ingredients include Tuf does not suggest that they are ineffective in preventing other diseases, but rather that they are more effective in preventing arthritis.

In one embodiment, when said active ingredients include NOX, MS53-0285 or a combination thereof, said symptoms caused by *Mycoplasma synoviae* infection are at least air sac lesion. Nevertheless, the fact that said active ingredients include NOX, MS53-0285 or a combination thereof does not suggest that they are ineffective in preventing other diseases, but rather that they are more effective in preventing air sac lesion.

In one embodiment, when said active ingredients include MS53-0285, said symptoms caused by *Mycoplasma synoviae* infection are at least tracheal lesion. Nevertheless, the fact that said active ingredients include MS53-0285 does not suggest that they are ineffective in preventing other diseases, but rather that they are more effective in preventing tracheal lesion.

In one embodiment, when said active ingredients include Tuf, NOX and MS53-0285, said symptoms caused by *Mycoplasma synoviae* infection are at least tracheal lesion, air sac lesion and arthritis.

In another aspect, the present disclosure relates to a cocktail vaccine used for preventing or treating *Mycoplasma synoviae* infection. The cocktail vaccine as described herein contains two and more antigens. In a preferred embodiment, the cocktail vaccine as described herein contains two and more antigens from the same type of disease-causing microorganism. In general, combining two or more antigens in a single vaccine does not necessarily contribute synergistically to the immunity-inducing effect of the vaccine. Instead, it may lead to an unfavorable consequence that the immunity-inducing effects of two or more antigens offset each other. In terms of cost, even if the immunity-inducing effects of two or more antigens do no offset each other, it is not worthwhile combining these two or more antigens in a single vaccine when there is no synergistic effect.

In a preferred embodiment, the active ingredients of said cocktail are at least two proteins selected from the group consisting of the following proteins: Tuf, NOX and MS53-0285. More preferably, said active ingredients include Tuf, NOX and MS53-0285. In a possible embodiment, as long as the antigen determinants on the folding from said amino acid sequences are not destroyed, said active ingredients may be fusion proteins having any two or more of said amino acid sequences. In another possible embodiment, said cocktail vaccine uses said proteins that are independent of each other.

In a preferred embodiment, the composition of the present disclosure further comprises a pharmaceutically acceptable adjuvant and/or a pharmaceutically acceptable additive. Said pharmaceutically acceptable adjuvant is used for enhancing the immunity-inducing effect of active ingredients, maintaining the stability of active ingredients, and enhancing the safety of said composition when used as a vaccine. Said pharmaceutically acceptable adjuvant is, including without limitation, a complete or incomplete Freund's adjuvant, alumina gel, surfactant, polyanion adjuvant, peptide, oil emulsion, or a combination thereof. Said pharmaceutically acceptable additive may be, including without limitation, a solvent, stabilizer, diluent, preservative, antibacterial agent, antifungal agent, isotonic agent, absorption delaying agent, or a combination thereof.

In a possible embodiment, the composition of the present disclosure can be made into formulations that are administered orally, nasally, intravenously, intramuscularly or intraperitoneally. In a possible embodiment, the active ingredients in the composition of the present disclosure have a concentration of 40 to 900 μg/mL based on the total volume of said composition. In another possible embodiment, the active ingredients in the composition of the present disclosure have a concentration of 40 to 600 μg/mL based on the total volume of said composition. In the cocktail vaccine of the present invention, the concentration of said active ingredients is the total concentration of all the antigens contained in said cocktail vaccine. In one embodiment, for example, when the cocktail vaccine of the present disclosure contains said Tuf antigens and said NOX antigens as active ingredients, said "concentration of active ingredients" is the total of the concentration of said Tuf antigens and that of said NOX antigens. In another embodiment, when the cocktail vaccine of the present disclosure contains said Tuf antigens, said NOX antigens and said MS53-0285 as active ingredients, said "concentration of active ingredients" is the total of the concentration of said Tuf antigens, that of said NOX antigens, and that of MS53-0285 antigens.

On the other hand, an obstacle to express said active ingredients in prokaryotic expression systems is to purify the expressed active ingredients from the said prokaryotic expression systems. Recombinant proteins expressed in prokaryotic expression systems are typically non-soluble, thereby making the purification process more difficult and costly. In this regard, one advantage of the antigen expression vector of the present disclosure is the ability to express soluble recombinant antigens, thereby simplifying the purification process and reducing its costs.

Thus, in another aspect, the present disclosure relates to an expression vector, which is used for producing said Tuf, NOX or MS53-0285. The expression vectors of the present disclosure comprise nucleotide sequences, expression elements and fusion partner sequences. Said nucleotide sequences can be translated as Tuf, NOX, MS53-0285 or a combination thereof.

Said expression elements refer to elements required for initiating transcription and translation processes in the expression system. Said expression elements should at least include a promoter and a ribosome binding site. Preferably, said expression elements may further include: an operator, enhancer sequences for enhancing translation/transcription, or a combination thereof. In a preferred embodiment, said expression vector is used in an *E. coli* expression system, and said expression elements can be recognized by *E. coli*.

In a preferred embodiment, the research of the present disclosure has proved that DsbC from *E. coli*, MsyB from *E. coli*, FklB from *E. coli*, or a combination thereof is preferably used as a fusion partner for expression of said antigens of the present invention, thereby making the recombinant proteins produced in a prokaryotic expression system as soluble form. In a preferred embodiment, in order to facilitate the purification process, said expression vector may further comprise a sequence encoding His-tag, GST-tag or a combination thereof, so that the obtained recombinant proteins can be purified using a nickel ion affinity column or a glutathione affinity column.

In yet another aspect, the present disclosure relates to a use of composition, in which said Tuf, NOX or MS53-0285 are used, for preventing and treating *Mycoplasma synoviae* infection. No further elaboration is needed for said composition for preventing and treating *Mycoplasma synoviae* infection since it has been previously described.

The following examples describe the experiments carried out for the development of the present disclosure to further illustrate the features and advantages thereof. It should be understood that the examples listed below are merely exemplary of the invention, and should not be used to limit the scope of the claims.

Example 1: Cloning of *Mycoplasma synoviae* Genes

Gene-specific primers are designed for various antigens (Table 1). A genomic DNA of *Mycoplasma synoviae* was used as a template and gene-specific primers were combined to amplify target genes.

TABLE 1

Primer pairs used for amplifying target genes

| Target gene | Primer sequence<br>Primer sequence (5' to 3') |
|---|---|
| tuf | TUFBAMHIF (SEQ ID NO: 10):<br>GATATA*GGATCC*ATGGCAAAATTAGATTTTGACCGTT<br>TUFSALIR (SEQ ID NO: 11):<br>CAATAT*GTCGAC*TTTAACGATTTTTGTAACTGATCCGG |
| nox | NOXBAMHIF (SEQ ID NO: 12):<br>GATATA*GGATCC*ATGGAAAACAAAAAAATTATAGTTGTTGGT<br>NOXSALIR (SEQ ID NO: 13):<br>CAATAT*GTCGAC*AGCTTTATATTTTAAACCAAGTGCTCTTAAA |

TABLE 1-continued

Primer pairs used for amplifying target genes

| Target gene | Primer sequence Primer sequence (5' to 3') |
|---|---|
| ms53-0285 | MS53BAMHIF (SEQ ID NO: 14): GATATA*GGATCC*ATGAATAAAACAAAAATTAAATTTATTTAGGAA<br>MS53SALIR (SEQ ID NO: 15): CAATAT*GTCGAC*ATTATTATTTGAACCAAATGTATCTCTAAATGA |

*GGATCC: BamHI cleavage site; GTCGAC: SalI cleavage site

1. Extracting Genomic DNA of *Mycoplasma synoviae*

The genomic DNA of *Mycoplasma synoviae* WVU 1853 (American Type Culture Collection® 25204™) was extracted using a DNA purification kit (Tissue & Cell Genomic DNA Purification kit; GMbiolab, Taiwan). First, 4.5 mL of the liquid culture of *Mycoplasma synoviae* was added into a centrifuge tube. After centrifugation (5,870×g, 5 minutes), the supernatant was removed and the pellet was collected. Then, 20 μL of proteinase K (10 mg/mL) and 200 μL of extraction reagent were added and allowed to react at 56° C. for 3 hours. 200 μL of binding solution was added and allowed to react at 70° C. for 10 minutes. When the reaction was completed, 200 μL of absolute alcohol was added and the mixture was transferred into a micro-centrifuge tube to be mixed thoroughly. The resulting solution (including precipitates) was pipetted into a spin column and the spin column was then put into a collection tube. After centrifugation (17,970×g) for 2 minutes, the supernatant was removed and 300 μL of binding solution was added again into the spin column. After centrifugation (17,970×g) for 2 minutes, the supernatant was removed. 700 μL of wash solution was added into the spin column and the mixture was centrifuged (17,970×g) for 2 minutes, and then the supernatant was removed, with the above steps being repeated once. Finally, the mixture was centrifuged at 17,970×g for 5 minutes to remove residual alcohol. The spin column was put into a sterilized micro-centrifuge tube and an appropriate amount of sterile deionized water was added to drain the genomic DNA.

2. Amplifying Target Genes Using Polymerase Chain Reaction (PCR)

The genomic DNA of *Mycoplasma synoviae* was used as a template and primers designed for tuf gene, nox gene, and ms53-0285 gene were used for PCR reaction, respectively. Primers used in PCR and PCR reaction conditions are shown in Table 2 below (primer sequences are shown in Table 1), wherein 50 μL of PCR reaction mixture contained 1×GDP-HiFi PCR buffer B, 200 μM of mixture of dATP, dTTP, dGTP, and dCTP, 1 μM of amplification primers, 200 ng of *Mycoplasma synoviae* genomic DNA and 1 U of GDP-HiFi DNA polymerase. After the completion of the PCR reaction, gel electrophoresis was conducted to confirm the existence of the DNA fragments with expected sizes.

TABLE 2

| PCR reaction conditions and primer pairs | | |
|---|---|---|
| Target gene | Primer pair | Reaction conditions |
| tuf | TUFBAMHIF TUFSALIR | 96° C. for 5 minutes; 94° C. for 30 seconds, 55° C. for 30 seconds, 68° C. for 45 seconds (35 cycles); 68° C. for 5 minutes |

TABLE 2-continued

| PCR reaction conditions and primer pairs | | |
|---|---|---|
| Target gene | Primer pair | Reaction conditions |
| nox | NOXBAMHIF NOXSALIR | 96° C. for 5 minutes; 94° C. for 30 seconds, 55° C. for 30 seconds, 68° C. for 45 seconds (35 cycles); 68° C. for 5 minutes |
| ms53-0285 | MS53BAMHIF MS53SALIR | 96° C. for 5 minutes; 94° C. for 30 seconds, 55° C. for 30 seconds, 68 C. for 1 minute and 15 seconds (35 cycles); 68° C. for 5 minutes |

3. Recovery and Cloning PCR Products

The recovery of the PCR products was carried out using the PCR Clean Up system kit (GMbiolab, Taiwan) and following the operations manual. Cloning of the target gene was then carried out using the CloneJET PCR Cloning Kit according to the manufacturer's operations manual. The ligation mixture was transformed into *E. coli* strain ECOS™ 9-5. The conditions of transformation are provided in the manual or may be modified based on standard experimental procedures in the art.

The bacteria transformed were cultured on LB solid medium containing ampicillin (100 μg/mL). After the formation of colonies, a colony PCR was conducted to screen the strains. First, lx Taq reaction buffer, 200 μM dNTP (dATP, dTTP, dGTP and dCTP), 1 μM amplification primers and 2.5 U DreamTaq DNA polymerase (Thermo, USA) were mixed to formulate 100 μL PCR reagent. After mixing, the PCR mixture was distributed to several PCR tubes (10 μL/tube). Colonies on the plates were picked into the PCR tubes for PCR reaction. The conditions for PCR reaction are: 95° C. for 5 minutes; 95° C. for 30 seconds, 55° C. for 30 seconds, 72° C. for X minutes (25 cycles); 72° C. for 7 minutes, wherein "X" was determined by the extension time required for the DNA polymerase. The time for tuf gene and nox gene was set as 1 minute 30 seconds, and the time for ms53-0285 gene was set as 2 minutes 30 seconds. After the PCR reaction, gel electrophoresis was conducted to confirm the PCR results. Colony PCR was used to confirm that recombinant plasmids in the transformed strains had insert DNA, and plasmids therein were then extracted for DNA sequencing (Tri-I Biotech, Inc.). The plasmids having tuf gene, nox gene and ms53-0285 gene were named as pJET-TUF, pJET-NOX and pJET-MS53, respectively.

4. Site-Directed Mutagenesis of Nox Gene nox gene has three TGA codons. TGA codons can be translated as tryptophan in *Mycoplasma* spp., and as stop codons in *E. coli*. In order to avoid failure to produce intact proteins using *E. coli* expression system, point mutations at TGA codons in nox gene must be induced, in order to replace said codons with those (TGG) that can be recognized by *E. coli* and translated as tryptophan.

Criteria for designing mutagenic primers included centering the mutation in the middle of the primer with a Tm of at least 78° C. The Tm value of the primer was calculated using the following formula provided by Invitrogen:

$$Tm=81.5+0.41(\%\ GC)-675/N-\%\ mismatch,$$

where "% GC" is the percentage of G or C nucleotides in the primer; "N" is the length of the primer; and "% mismatch" is the percentage of mutated bases in the primer. The primers used for point mutation of nox gene are listed in Table 3 below, including NOXBAMHIF/NOXM2, NOXM1/NOXM4, NOXM3/NOXM6 and NOXM5/NOXSALIR.

amplification using NOXBAMHIF/NOXSALIR primer pair. The PCR reaction condition was: 96° C. for 2 minutes; 94° C. for 30 seconds, 55° C. for 30 seconds, 68° C. for 45 seconds (35 cycles); 68° C. for 5 minutes.

TABLE 3

Primers used for point mutation in nox gene

| Primer | Primer sequence (5' to 3') |
|---|---|
| NOXBAMHIF | SEQ ID NO: 16<br>GATATAGGATCCATGGAAAACAAAAAAATTATAGTTGTTGGT |
| NOXM2 | SEQ ID NO: 17<br>CTTTAAACATTCCTCCAACGCAAACAGCAATACCACATC |
| NOXM1 | SEQ ID NO: 18<br>GATGTGGTATTGCTGTTTGCGTTGGAGGAATGTTTAAAG |
| NOXM4 | SEQ ID NO: 19<br>GGAGGAACTATAGGGCATGTTCCTCCAGC |
| NOXM3 | SEQ ID NO: 20<br>GCTGGAGGAACATGCCCTATAGTTCCTCC |
| NOXM6 | SEQ ID NO: 21<br>CATGAGAATCTTGTCCCCAAGAACCAACTTGAG |
| NOXM5 | SEQ ID NO: 22<br>CTCAAGTTGGTTCTTGGGGACAAGATTCTCATG |
| NOXSALIR | SEQ ID NO: 23<br>CAATATGTCGACAGCTTTATATTTTAAACCAAGTGCTCTTAAA |

The 50 μL of PCR mixture contained 1×GDP-HiFi PCR buffer B; 200 μM of mixture of dATP, dTTP, dGTP, and dCTP; 1 μM of amplification primer; 100 ng of pJET-NOX and 1 U GDP-HiFi DNA polymerase. The PCR reaction condition was: 98° C. for 2 minutes; 94° C. for 30 seconds, 55° C. for 30 seconds, 68° C. for 30 seconds (35 cycles); 68° C. for 5 minutes.

After the PCR reaction, gel electrophoresis was conducted to confirm the existence of the DNA fragments with expected sizes. The PCR products were collected using Gel-M™ gel extraction system kit. The four PCR products collected were used as templates for gene Following this step, a full-length point-mutated nox gene was obtained. PCR product was collected using PCR Clean Up kit.

5. Site-Directed Mutagenesis of Ms53-0285 Gene ms53-0285 gene has six TGA codons. The primers used for point mutation of ms53-0285 gene are listed in Table 4 below, including MS53BAMHIF/MS53M2, MS53M1/MS53M4, MS53M3/MS53M6, MS53M5/MS53M8, MS53M7/MS53M10, MS53M9/MS53M12 and MS53M11/MS53SALIR.

TABLE 4

Primers used for point mutation in ms53-0285 gene

| Primer | Primer sequence (5' to 3') |
|---|---|
| MS53BAMHIF | SEQ ID NO: 24<br>GATATAGGATCCATGAATAAAACAAAAATTAAATTTATTTTAGGAA |
| MS53M2 | SEQ ID NO: 25:<br>GTTATCGACTGGATCACCGCATTGCTTTTGAATTTGAC |
| MS53M1 | SEQ ID NO: 26<br>GTCAAATTCAAAAGCAATGCGGTGATCCAGTCGATAAC |
| MS53M4 | SEQ ID NO: 27<br>CTATCACTTTGTTGCAATAACAATAATTGCAATTACTTGTATCGTTTTTAATTTTATC |
| MS53M3 | SEQ ID NO: 28<br>GATAAAATTAAAAACGATACAAGTAATTGCAAATTATTGTTATTGCAACAAAGTGATAG |

TABLE 4-continued

Primers used for point mutation in ms53-0285 gene

| Primer | Primer sequence (5' to 3') |
|---|---|
| MS53M6 | SEQ ID NO: 29<br>CTAGTAATTTAATATATTTTTCGCAATCAGCTTTAACTGGATTTG |
| MS53M5 | SEQ ID NO: 30<br>CAAATCCAGTTAAAGCTGATTGGGAAAAAATATATTAAATTACTAG |
| MS53M8 | SEQ ID NO: 31<br>GAATTTTTTGCTGAATTTTCATTGCATTTTGTTGGAGCATTTATTAC |
| MS53M7 | SEQ ID NO: 32<br>GTAATAAATGCTCCAACAAAATGCAATGAAAATTCAGCAAAAAATTC |
| MS53M10 | SEQ ID NO: 33<br>CTTTCTTAGAAGTTACAAGCCAATGTACAAATGCTCTAG |
| MS53M9 | SEQ ID NO: 34<br>CTAGAGCATTTGTACATTGGCTTGTAACTTCTAAGAAAG |
| MS53M12 | SEQ ID NO: 35<br>CTGGTGATTCATATGTAGTCCAGTTTGCTTGATCTTTTG |
| MS53M11 | SEQ ID NO: 36<br>CAAAAGATCAAGCAAACTGGACTACATATGAATCACCAG |
| MS53SALIR | SEQ ID NO: 37<br>CAATATGTCGACATTATTATTTGAACCAAATGTATCTCTAAATGA |

The 50 μL of PCR mixture contained 1×GDP-HiFi PCR buffer B; 200 μM of mixture of dATP, dTTP, dGTP, and dCTP; 1 μM of amplification primer; 100 ng of pJET-MS53 and 1 U GDP-HiFi DNA polymerase. The PCR reaction condition was: 96° C. for 2 minutes; 94° C. for 30 seconds, 55° C. for 30 seconds, 68° C. for 30 seconds (35 cycles); 68° C. for 5 minutes.

After the PCR reaction, gel electrophoresis was conducted to confirm the existence of the DNA fragments with expected sizes. The PCR products were collected using Gel-M™ gel extraction system kit. The seven PCR products collected were used as templates for gene amplification using MS53BAMHIF/MS53SALIR primer pair. The PCR reaction condition was: 96° C. for 2 minutes; 94° C. for 30 seconds, 55° C. for 30 seconds, 68° C. for 1 minute and 15 seconds (35 cycles); 68° C. for 5 minutes. Following this step, a full-length point-mutated ms53-0285 gene was obtained. PCR product was collected using PCR Clean Up kit.

Following the above operations, tuf gene (SEQ ID NO: 04), nox gene (SEQ ID NO: 05) and ms53-0285 gene (SEQ ID NO: 06) were obtained. They can be translated as Tuf (SEQ ID NO: 01), NOX (SEQ ID NO: 02) and MS53-0285 (SEQ ID NO: 03), respectively.

Example 3: Constructing *Mycoplasma synoviae* Antigen Expression Plasmids

Plasmids having dsbC gene of *E. coli* were used as backbone for constructing *Mycoplasma synoviae* antigen expression plasmids. The construction processes of expression plasmids are as follows:

1. Construction of Tuf Expression Vector

Amplified tuf gene was cut with BamHI and SalI and the resulting DNA fragment was joined by T4 DNA ligase with a DsbC fusion expression plasmid pET-HISDsbC pre-cut by the same restriction enzymes. The ligation product was then transformed into *E. coli* ECOS 9-5. Transformants were screened by colony PCR. Gel electrophoresis was conducted to confirm the existence of the amplified DNA fragment with the expected size. When it was confirmed that the transformants contained inserted DNA in their recombinant plasmids, the plasmids were extracted out for DNA sequencing. The plasmids having the correct DNA sequence were named as pET-HISDsbC-MSTUF (SEQ ID NO: 07).

2. Construction of NOX Expression Plasmid

Mutated nox gene was cut with BamHI and SalI and the resulting DNA fragment was joined by T4 DNA ligase with a DsbC fusion expression plasmid pET-DsbC pre-cut by the same restriction enzymes. The ligation product was then transformed into *E. coli* ECOS 9-5. Transformants were screened by colony PCR. Gel electrophoresis was conducted to confirm the existence of the amplified DNA fragment with the expected size. When it was confirmed that the transformants contained inserted DNA in their recombinant plasmids, the plasmids were extracted out for DNA sequencing. The plasmids having the correct DNA sequence were named as pET-DsbC-MSNOX (SEQ ID NO: 08).

3. Construction of MS53-0285 Expression Plasmid

Mutated ms53-0285 gene was cut with BamHI and SalI and the resulting DNA fragment was joined by T4 DNA ligase with a DsbC fusion expression plasmid pET-DsbC pre-cut by the same restriction enzymes. The ligation product was then transformed into *E. coli*

ECOS 9-5. Transformants were screened by colony PCR. Gel electrophoresis was conducted to confirm the existence of the amplified DNA fragment with the expected size. When it was confirmed that the transformants contained inserted DNA in their recombinant plasmids, the plasmids were extracted out for DNA sequencing. The plasmids having the correct DNA sequence were named as pET-DsbC-MS53 (SEQ ID NO: 09).

Example 4: Expressing and Purifying Recombinant *Mycoplasma synoviae* Antigens The plasmids for expressing *Mycoplasma synoviae* antigens were transformed into *E. coli* BL21 (DE3), respectively. A single colony of the strain expressing the antigens was selected and inoculated in 12 mL of LB medium containing kanamycin (final concentration: 30 μg/mL). The resulting mixture was cultured overnight at 37° C. and at 180 rpm. Then, 10 mL of the liquid culture was added to 1 L of LB medium containing kanamycin (final concentration: 30 μg/mL) and was shake-cultured (37° C., 180 rpm) until $OD_{600}$ reached about 0.4-0.6. 0.1 mM IPTG was then added at 28° C. to induce protein expression. After for 4 hours of induction, the culture was centrifuged (10,000×g, 10 minutes, 4° C.) and bacterial cell pellet was collected. The bacterial cell pellet was resuspended in 10 mL of phosphate buffer (20 mM sodium phosphate, 500 mM NaCl, pH 7.4) and was disrupted by ultrasonication. The suspension was centrifuged (30,966×g, 30 min) and the supernatant was collected. Finally, the supernatant was filtered through a filter membrane with 0.22 μM pore size. Protein electrophoresis was conducted to observe the expression status and solubility of the recombinant antigens.

Protein purification was then conducted using immobilized-metal ion affinity chromatography by way of the covalent bonding between His tag on the recombinant antigens and nickel ions or cobalt ions. The recombinant antigens were purified by ÄKTA prime plus (GE Healthcare, Sweden) equipped with 5 mL HiTrap™ Ni excel column (GE Healthcare, Sweden). First, said supernatant was introduced into HiTrap™ Ni excel column after the column was equilibrated with 25 mL of phosphate buffer solution. After the sample was fully introduced, 100 mL of a wash buffer solution containing 30 mM imidazole (20 mM sodium phosphate, 500 mM NaCl, 30 mM imidazole, pH 7.4) was used to wash the column to remove non-specific proteins adhered thereon. Finally, 150 mL of an elution buffer solution containing 250 mM imidazole (20 mM sodium phosphate, 500 mM NaCl, 250 mM imidazole, pH7.4) was used to wash off the recombinant antigens from the resin, wherein imidazole of high concentration can compete with the recombinant antigens for binding sites on the resin, thereby causing the recombinant antigens to be washed off. The purified antigen solution was put into Amico™ ultra-15 ultracel-30K centrifuge tube (Merck Millipore, USA) to be centrifuged (2,600×g) at 4° C. until it reached an appropriate volume, and was then stored at 4° C. for further use.

The result is shown in FIG. 1. It can be observed from FIG. 1A that the expression antigens of this example have excellent solubility so as to be subsequently purified and commercialized. FIG. 1B shows that the antigens obtained through purification have reliable purity.

Example 5: Single-Antigen Vaccine Production and Chicken Experiments 4-week-old specific pathogen-free chickens (purchased from the Animal Drugs Inspection Branch of the Animal Health Research Institute, Council of Agriculture, Executive Yuan, Taiwan) were used and kept in animal house facilities at the inspection branch. Recombinant *Mycoplasma synoviae* antigens Tuf, NOX and MS53-0285 were mixed individually with a commercially available adjuvant MONTANIDE™ Gel 01 (Seppic) following the operations manual, so that the final dose of each single-antigen vaccine became 50 μg/0.5 mL. 0.5 mL of these single-antigen vaccines were administered subcutaneously in the back of the neck of 4-week-old chickens. Second vaccination was conducted to chickens reaching 6 weeks of age. After vaccination, the chickens were observed for two weeks. Blood samples were then collected and centrifuged (2,000×g, 4° C., 15 minutes) to obtain serum samples. *Mycoplasma synoviae* antibodies were assayed using a commercial kit (IDEXX *Mycoplasma synoviae* Antibody Test Kit).

The results are shown in Table 5 below and in FIG. 2. The specific antibodies in serum of chickens administered with single-antigen vaccines of Tuf, NOX and MS53_0285 according to the present invention were all positive, with a positive rate of 57%, 71% and 75%, respectively.

TABLE 5

Positive rates of single-antigen vaccines

| Score | Group<br>Control group | Tuf | NOX | MS53-0285 |
|---|---|---|---|---|
| S/P ratio < 0.5 | 7 | 3 | 2 | 2 |
| S/P ratio > 0.5 | 0 | 4 | 5 | 6 |
| S/P positive rate (%) | 0 | 57 | 71 | 75 |

Next, 8-week-old chickens were challenged with *Mycoplasma synoviae* through tracheae and footpads. The challenge strain used was ATRI 2014 (hereinafter "MS-f1"), which was isolated from commercial native chicken farm in Taiwan. The challenge strain was cultured in *Mycoplasma* medium at 32° C. and at 75 rpm for 32 hours.

In trachea challenge, the chickens were held and a feeding tube was inserted into the trachea of the chickens. 1 mL of broth of challenge strain with $10^6$ CCU was then injected using a syringe. Finally, the necks of the chickens were rubbed gently so that the broth could be spread out evenly. In footpad challenge, footpads were disinfected with alcohol wipes and 0.5 mL of broth of challenge strain with $10^3$ CCU was injected therein using a needle. After challenge, blood samples were collected and serum was isolated to assess *Mycoplasma synoviae*-specific antibodies. Weight, footpad temperature and footpad thickness of the chickens at various time points were also recorded. At the end of the experiment, a dissection was performed to observe the symptoms of tracheae, air sac and footpad swelling among the chickens. Observed results were recorded following the diagnostic criteria for organ dysfunction as described in Table 6 below.

TABLE 6

Diagnostic criteria for organ dysfunction in poultry

Tracheal lesion index

| Score | Symptoms |
|---|---|
| 0 | No visible change. |
| 1 | Increased mucus; moderate mucosal blood stasis. |
| 2 | Increased mucus; mucosal blood stasis; cottage cheese-like discharge. |

TABLE 6-continued Diagnostic criteria for organ dysfunction in poultry

| | |
|---|---|
| 3 | Increased mucus; mucosal blood stasis; cottage cheese-like discharge. |

Air sac lesion index

| Score | Symptoms |
|---|---|
| 0 | No visible change. |
| 1 | Slightly cloudy or covered with small yellow cheese-like fiber protein spots. |
| 2 | Cloudy; slight thickened walls; covered with yellow substance. |
| 3 | Thicker walls; cloudy and opaque; covered with discharge forming yellow spots. |

Arthritis (footpad swelling)

| Score | Symptoms |
|---|---|
| 0 | No change compared to left footpad. |
| 1 | Mild swelling. |
| 2 | Increased swelling that causes creases on footpad surface to disappear. |
| 3 | Increased swelling that spreads to neighboring tissues. |
| 4 | More severe swelling; redness and cracked skin; watery discharge/pus oozing from swollen sites that are cut open. |

Figure 3:
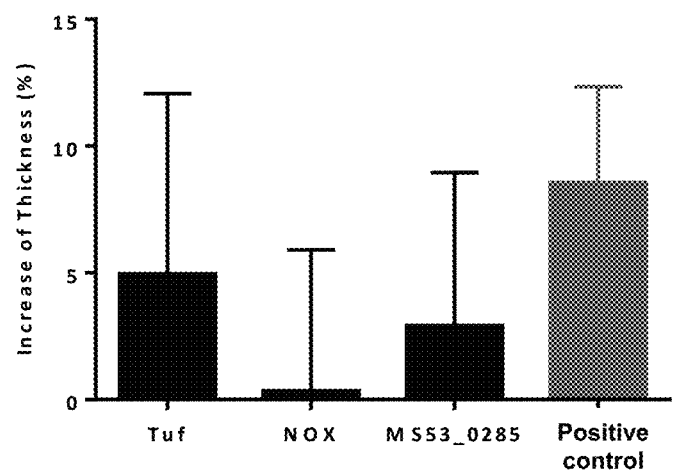
FIG. 3 shows the level of increase in footpad thickness of chickens infected with *Mycoplasma synoviae* in Example 5 of the present invention.
Figure 4:
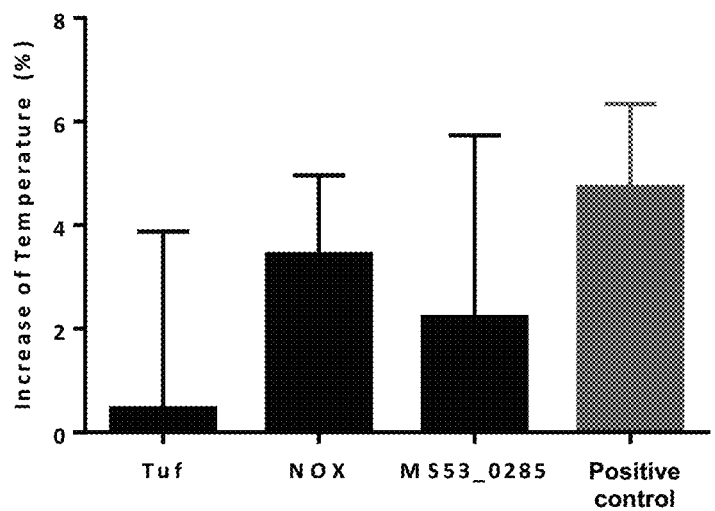
FIG. 4 shows the level of increase in footpad temperature of chickens infected with *Mycoplasma synoviae* in Example 5 of the present invention.
Figure 5:
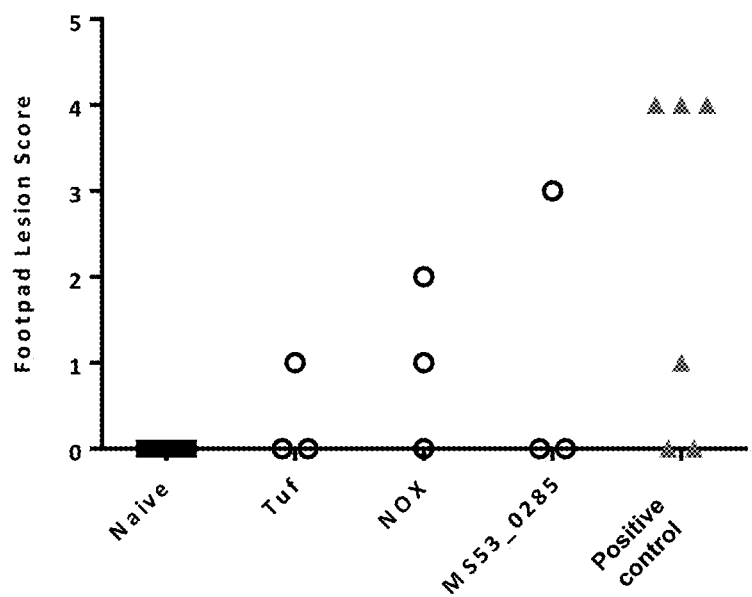
FIG. 5 shows the footpad infection scores of chickens infected with *Mycoplasma synoviae* in Example 5 of the present invention.

It could be observed from the footpad thickness of the chickens that the group of chickens administered with single-antigen vaccine had milder swelling than the positive group (see FIG. 3). On the other hand, the footpad temperature measurement results showed that the single-antigen vaccine of the present disclosure alleviated chicken footpad inflammation (FIG. 4). Further assessments and records of footpad infection showed that the chickens administered with the single-antigen vaccine of the present disclosure had less footpad infection levels, with Tuf vaccine being the most effective (FIG. 5).

Figure 6:
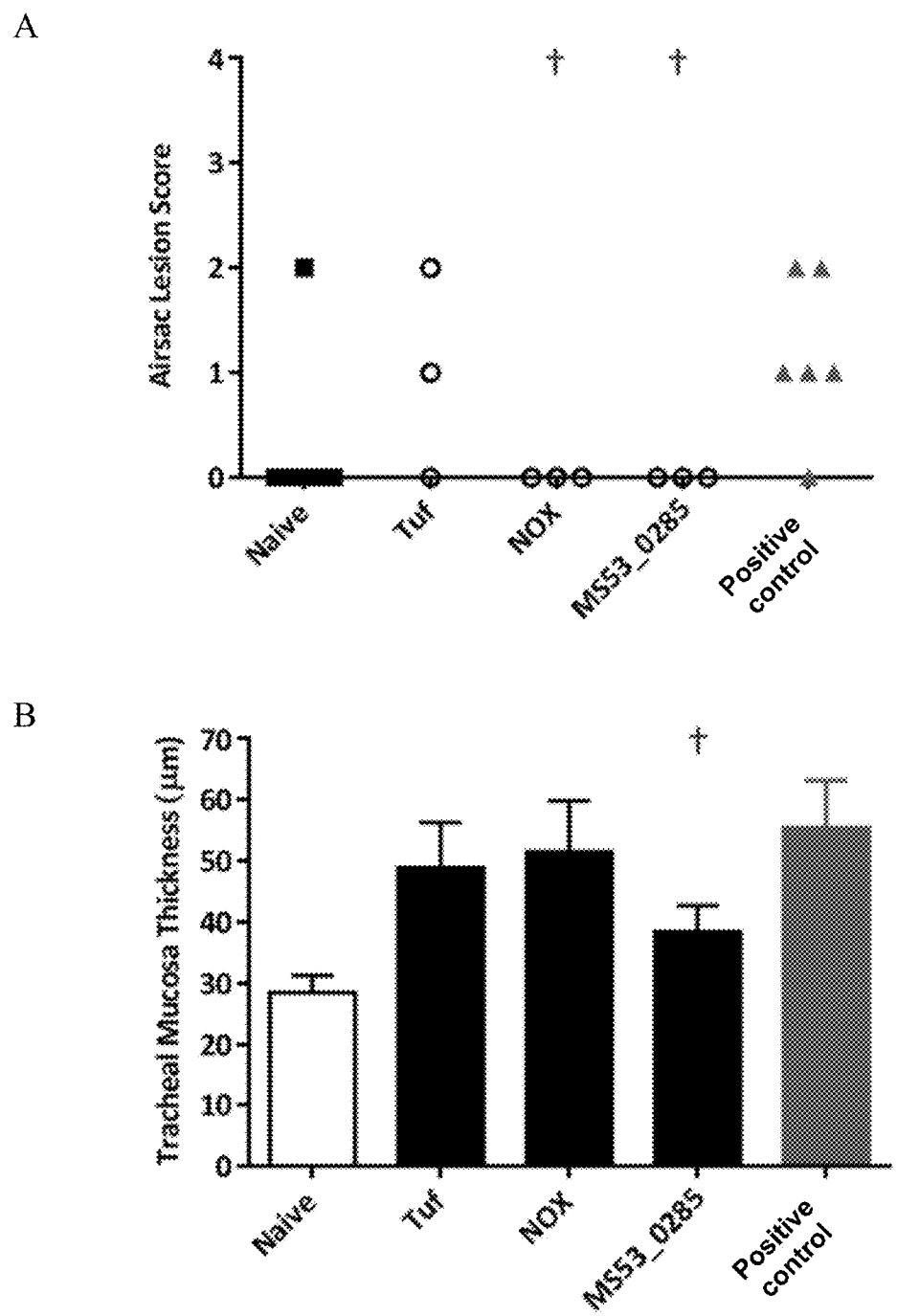
FIG. 6 shows (A) the air sac lesion scores of chickens infected with *Mycoplasma synoviae* in Example 5 of the present invention, and (B) tracheal mucosal thickness of chickens in Example 5. The statistics shows that the vaccines of the present disclosure are statistically significant compared to the (positive control group) (T-test, †: $p<0.1$).

Air sac lesion is another common type of infection as a result of *Mycoplasma synoviae* infection. Air sacs in healthy chicken should be transparent without being covered with discharges. FIG. 6A shows that among the chickens that had not been administered with said single-antigen vaccines, their air sacs thickened and were covered with yellow cheese-like fiber protein in a visible manner. On the other hand, air sac lesion could be effectively prevented by administering the single-antigen vaccine of the present invention. The results also showed that NOX and MS53-0285 vaccines were particularly effective in preventing air sac lesion.

Chicken tracheae were further sectioned. H&E staining was performed to observe the changes of mucus thickness on tracheal rings. The results showed that mucosal infection could be effectively prevented among the vaccinated groups, compared to the non-vaccinated challenge chickens, by administering the single-antigen vaccine of the present invention, with MS53-0285 subunit vaccine being the most effective (FIG. 6B).

It can be understood from the above results that despite slight differences in efficacy, Tuf, NOX and MS53-0285 vaccines of the present disclosure are generally effective in alleviating symptoms induced by *Mycoplasma synoviae*.

Example 6: Multi-Antigen Vaccine (Cocktail Vaccine) Production and Chicken Experiments 4-week-old specific pathogen-free chickens (purchased from the Animal Drugs Inspection Branch of the Animal Health Research Institute, Council of Agriculture, Executive Yuan, Taiwan) were used and kept in animal house facilities at the inspection branch. Various combinations of antigens (Tuf+NOX, Tuf+MS53-0285, NOX+MS53-0285 and Tuf+NOX+MS53-0285) were mixed individually with commercially available adjuvants to obtain cocktail vaccines. Each antigen in each dose of vaccine (0.5 mL) was 50 μg.

0.5 mL of said recombinant-antigen vaccine was administered subcutaneously in the back of the neck of 4-week-old chickens. Second vaccination was conducted to chickens reaching 6 weeks of age. After vaccination, the chickens were observed for two weeks. Blood samples were then collected and centrifuged (2,000×g, 4° C., 15 minutes) to obtain serum samples. *Mycoplasma synoviae*-specific antibodies were detected using a commercial kit (IDEXX *Mycoplasma synoviae* Antibody Test Kit).

Figure 7:
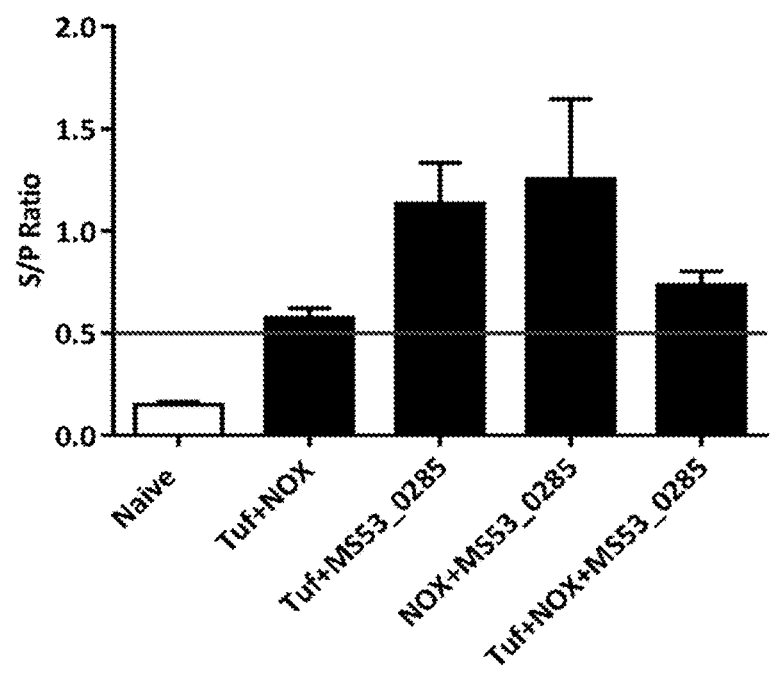
FIG. 7 shows the positive *Mycoplasma synoviae*-specific antibodies responses in the chicken serum of Example 6 of the present invention.

The results are shown in Table 7 below and in FIG. 7, suggesting that double-antigen and triple-antigen vaccines both improved antibody production levels in chickens. In other words, when used in combinations, recombinant antigens did not cause mutual interference; instead, they produced synergistic effect that could strengthen immunity-inducing potential.

TABLE 7

| | Score | | |
|---|---|---|---|
| Group | S/P ratio < 0.5 | S/P ratio > 0.5 | S/P positive rate (%) |
| Tuf + NOX | 3 | 4 | 57 |
| Tuf + MS53-0285 | 0 | 7 | 100 |
| NOX + MS53-0285 | 0 | 8 | 100 |
| Tuf + NOX + MS53-0285 | 1 | 7 | 88 |

Example 7: Multi-Antigen Vaccine (Cocktail Vaccine) Production and Chicken Experiments 4-week-old specific pathogen-free chickens (purchased from the Animal Drugs Inspection Branch of the Animal Health Research Institute, Council of Agriculture, Executive Yuan, Taiwan) were used and kept in animal house facilities at the inspection branch. The recombinant antigens Tuf, NOX and MS53-0285 were mixed with a commercially available adjuvant MONTANIDE™ ISA 71 VG (Seppic) to obtain the cocktail vaccine of the present invention. Each antigen in each dose of vaccine (0.5 mL) was 50 μg. Said adjuvant was mixed with said antigens at a 7:3 mix ratio by weight. Given that the specific gravity of said adjuvant is about 0.816, the vaccine produced in this experiment contained approximately 0.37 mL of adjuvant.

0.5 mL of said recombinant-antigen vaccine was administered subcutaneously in the back of the neck of 4-week-old chickens. Second vaccination was conducted to chickens reaching 6 weeks of age. After vaccination, the chickens were observed for two weeks. Blood samples were then collected and centrifuged (2,000×g, 4° C., 15 minutes) to obtain serum samples. *Mycoplasma synoviae*-specific antibodies were detected using a commercial kit (IDEXX *Mycoplasma synoviae* Antibody Test Kit).

Figure 8:
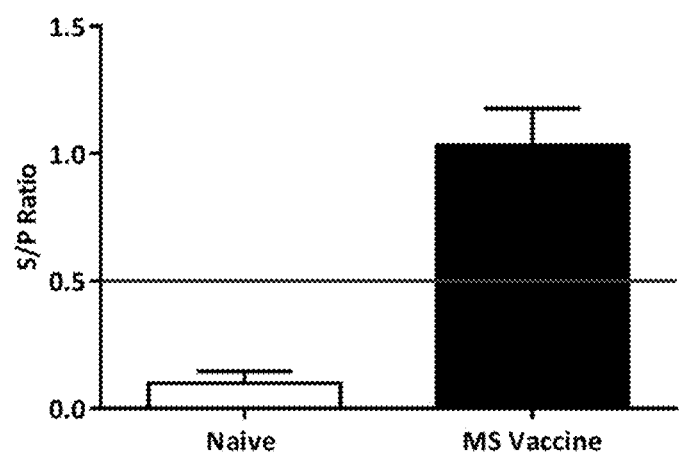
FIG. 8 shows the positive *Mycoplasma synoviae*-specific antibodies responses in the chicken serum of Example 7 of the present invention.

The results are shown in Table 8 below and in FIG. 8, suggesting that triple-antigen vaccines induced antibody production in chickens. In other words, when used in combinations, recombinant antigens did not cause mutual interference; instead, they produced synergistic effect that could strengthen immunity-inducing potential. These results are in line with those shown in FIG. 7.

TABLE 8

| Score | Group | |
|---|---|---|
| | Control group | Triple-antigen vaccine |
| S/P ratio < 0.5 | 8 | 1 |
| S/P ratio > 0.5 | 0 | 7 |
| S/P positive rate (%) | 0 | 88 |

Next, 8-week-old chickens were then challenged with *Mycoplasma synoviae* MS-f1 through tracheae and footpads. After the challenge, blood samples were collected and serum was isolated to assess *Mycoplasma synoviae*-specific antibodies. Weight, footpad temperature, and footpad thickness of each chicken at various time points were also recorded. At the end of the experiment, a dissection was performed to observe the symptoms of tracheae, air sac and footpad swelling among the chickens. Observed results were recorded following the diagnostic criteria for organ dysfunction as described in Table 6.

Figure 9:
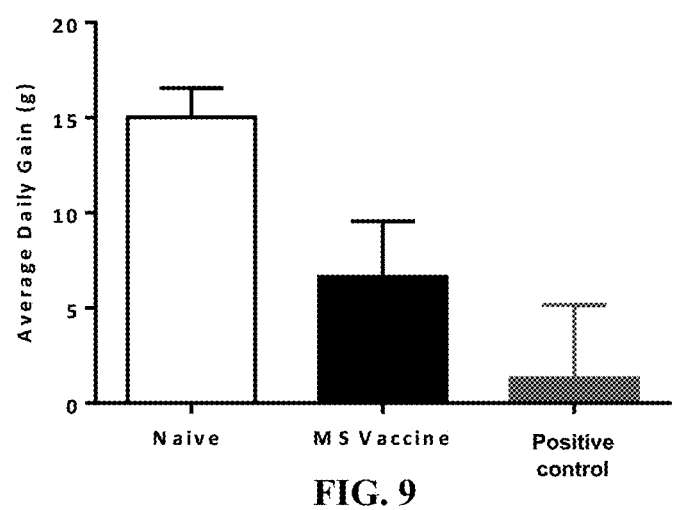
FIG. 9 shows the average daily gain of chickens infected with *Mycoplasma synoviae* in Example 7 of the present invention.
Figure 10:
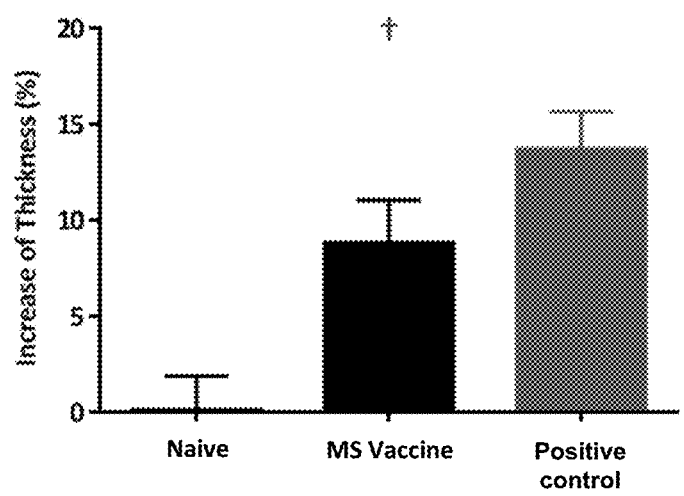
FIG. 10 shows footpad thickness changes displayed by chickens infected with *Mycoplasma synoviae* in Example 7 of the present invention. The statistics shows that the vaccines of the present disclosure are statistically significant compared to the positive control group (T-test, †: $p<0.1$).
Figure 11:
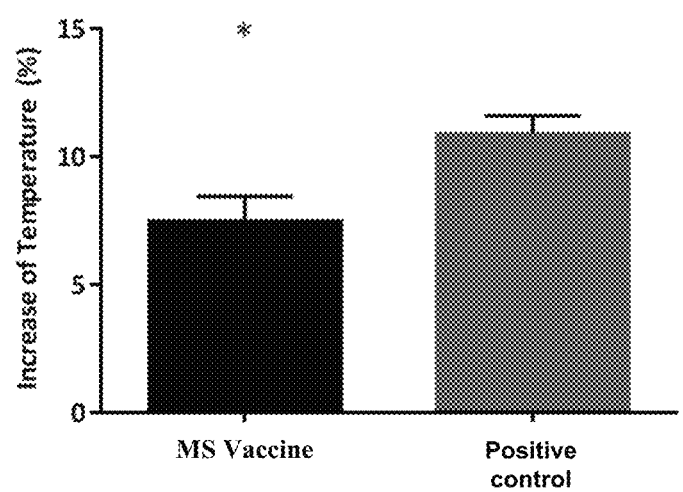
FIG. 11 shows footpad temperature changes displayed by chickens infected with *Mycoplasma synoviae* in Example 7 of the present invention. The statistics shows that the vaccines of the present disclosure are statistically significant compared to the positive control group (T-test, †: *: $p<0.05$).
Figure 12:
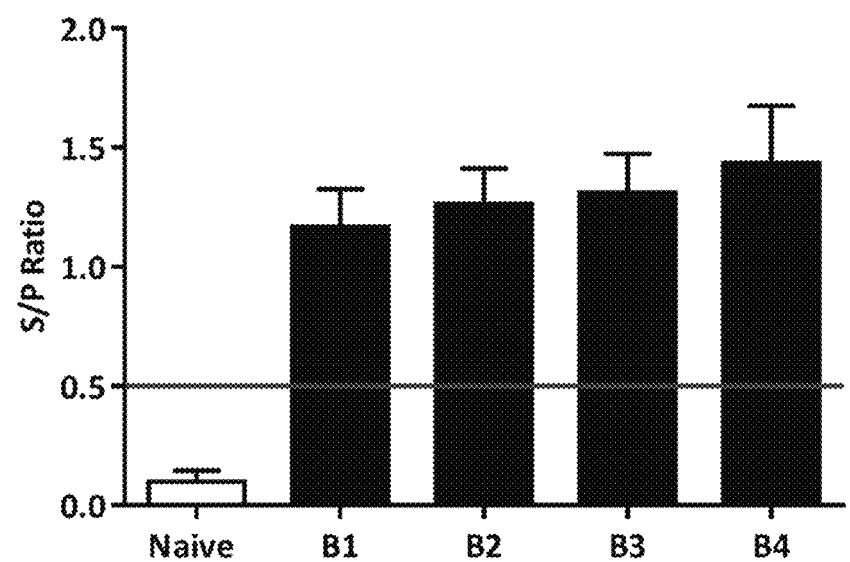
FIG. 12 shows the positive *Mycoplasma synoviae*-specific antibodies responses in the chicken serum of Example 8 of the present invention.

The results showed that the triple-antigen vaccine of the present disclosure could alleviate weight loss that occurred on infected chickens (FIG. 9). In addition, the triple-antigen vaccine was also effective in reducing symptoms regarding footpad swelling and temperature (FIGS. 10 and 11). The chickens were further sacrificed and dissected. It was observed from footpad and air sac lesion scores that the triple-antigen vaccine was effective in lowering the severity of footpad and air sac lesion. See Table 9 below.

TABLE 9

| Score | Group | | |
|---|---|---|---|
| | Naive | Triple-antigen vaccine | Challenge |
| Positive rate of footpad infection (%) | 0 | 88 | 100 |
| Positive rate of air sac lesion (%) | 0 | 50 | 88 |

Example 8: Dosage Test for Triple-Antigen Vaccine

The recombinant antigens were mixed with a commercially available adjuvant MONTANIDE™ ISA 71 VG (Seppic) to formulate subunit vaccines having recombinant antigens at four concentrations: 150 µg, 100 µg, 50 µs and 20 µs per dose (0.5 mL), respectively. Said adjuvant was mixed with said antigens at a 7:3 mix ratio by weight. Given that the specific gravity of said adjuvant is about 0.816, the vaccine produced in this experiment contained approximately 0.37 mL of adjuvant. Groups were designed as shown in Table 10.

TABLE 10

| Group | Naive | B1 | B2 | B3 | B4 | Challenge |
|---|---|---|---|---|---|---|
| Amount of each antigen per dose (µg/0.5 mL) | N/A | 150 | 100 | 50 | 20 | N/A |

4-week-old specific pathogen-free chickens (purchased from the Animal Drugs Inspection Branch of the Animal Health Research Institute, Council of Agriculture, Executive Yuan, Taiwan) were used and kept in animal house facilities at the inspection branch. Said recombinant-antigen vaccine was administered to the chickens twice every two weeks for vaccination. Two weeks after vaccination, the chickens were challenged with *Mycoplasma synoviae* MS-f1 through tracheae and footpads. After challenge, blood samples were collected and serum was isolated to assess *Mycoplasma synoviae*-specific antibodies. Weight, footpad temperature, and footpad thickness of the chickens at various time points were also recorded. At the end of the experiment, a dissection was performed to observe the symptoms of air sac lesion among the chickens. Observed results were recorded following the diagnostic criteria for organ dysfunction as described in Table 5.

Figure 13:
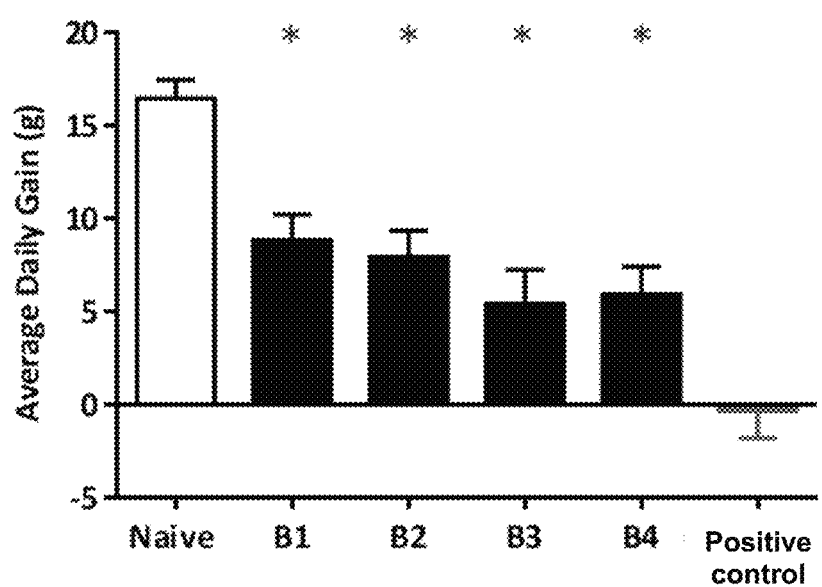
FIG. 13 shows the average daily gain of chickens infected with *Mycoplasma synoviae* in Example 8 of the present invention. The statistics shows that the vaccines of the present disclosure are statistically significant compared to the positive control group (T-test, †: *: $p<0.05$).
Figure 14:
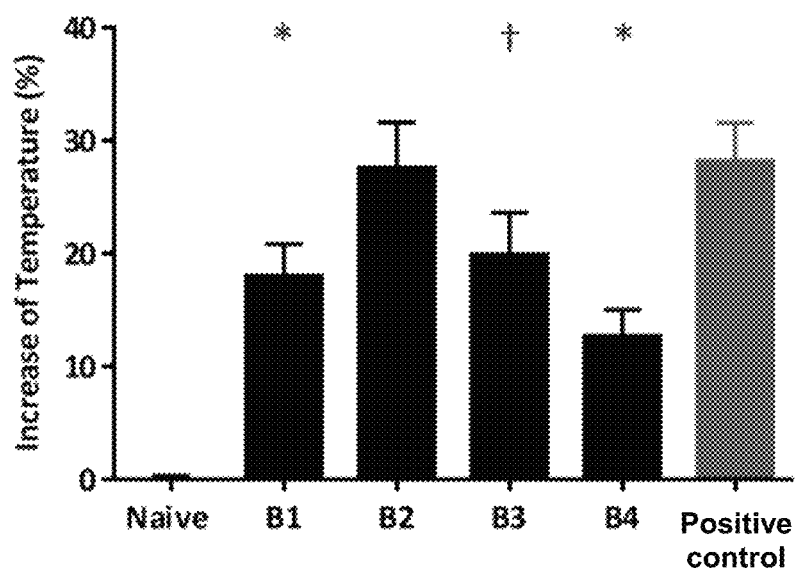
FIG. 14 shows footpad temperature changes displayed by chickens infected with *Mycoplasma synoviae* in Example 8 of the present invention. The statistics shows that the vaccines of the present disclosure are statistically significant compared to the positive control group (T-test, †: $p<0.1$; *: $p<0.05$).

The results showed that the four doses of antigen vaccines used in this experiment could all induce antibody production in the chickens. In addition, the four doses that were tested in this experiment were all effective in alleviating symptoms regarding weight and footpad temperature (FIGS. 13 and 14). The chickens were further sacrificed and dissected. It was observed from air sac lesion scores that the four doses of vaccines tested were all effective in ameliorating air sac lesion (see Table 12).

TABLE 11

| Score | Group | | | | |
|---|---|---|---|---|---|
| | Naive | B1 | B2 | B3 | B4 |
| S/P ratio < 0.5 | 10 | 1 | 0 | 0 | 0 |
| S/P ratio > 0.5 | 0 | 11 | 11 | 11 | 12 |
| S/P positive rate (%) | 0 | 92 | 100 | 100 | 100 |

TABLE 12

| Score | Group | | | | | |
|---|---|---|---|---|---|---|
| | Naive | B1 | B2 | B3 | B4 | Challenge |
| 0 | 12 | 3 | 3 | 4 | 6 | 1 |
| 1 | 0 | 3 | 0 | 3 | 4 | 0 |
| 2 | 0 | 3 | 5 | 3 | 1 | 5 |
| 3 | 0 | 2 | 2 | 0 | 1 | 6 |
| Positive rate of air sac lesion (%) | 0 | 73 | 70 | 60 | 50 | 92 |

What is claimed is:
1. A composition for alleviating symptoms caused by *Mycoplasma synoviae* infection, comprising:
at least two polypeptides selected from the group consisting of SEQ ID NO: 01 (Tuf), SEQ ID NO: 02 (NOX), and SEQ ID NO: 03 (M553-0285); and
a pharmaceutically acceptable adjuvant.

2. The composition of claim 1, wherein said composition comprises SEQ ID NO: 01, SEQ ID NO: 02, and SEQ ID NO: 03.

3. The composition of claim 1, wherein said at least two polypeptides selected from the group consisting of SEQ ID NO: 01 (Tuf), SEQ ID NO: 02 (NOX), and SEQ ID NO: 03 (MS53-0285) have a concentration of 40 µg/mL to 900 µg/mL based on the total volume of said composition.

4. The composition of claim 1, wherein said pharmaceutically acceptable adjuvant comprises a complete or incomplete Freund's adjuvant, alumina gel, surfactant, polyanion adjuvant, peptide, oil emulsion, or a combination thereof.

5. The composition of claim 1, said composition further comprising a pharmaceutically acceptable additive.

6. The composition of claim 5, wherein said pharmaceutically acceptable additive comprises a solvent, stabilizer, diluent, preservative, antibacterial agent, antifungal agent, isotonic agent, absorption delaying agent, or a combination thereof.

7. The composition of claim 1, wherein said symptoms caused by *Mycoplasma synoviae* infection are tracheal lesion, air sac lesion, arthritis or a combination thereof.

8. The composition of claim 7, wherein said symptoms caused by Mycoplasma synoviae infection are at least arthritis provided that the composition includes SEQ ID NO: 01.

9. The composition of claim 7, wherein said symptoms caused by
*Mycoplasma synoviae* infection are at least air sac lesion provided that the composition includes SEQ ID NO: 02 and/or SEQ ID NO: 03.

10. The composition of claim 7, wherein said symptoms caused by *Mycoplasma synoviae* infection are at least tracheal lesion provided that the composition includes SEQ ID NO: 03.

11. The composition of claim 2, wherein said symptoms caused by *Mycoplasma synoviae* infection are tracheal lesion, air sac lesion and arthritis.

12. An expression vector, comprising:
the nucleotide sequence of at least two selected from the group consisting of SEQ ID NO: 4, SEQ ID NO: 5, and SEQ ID NO: 6;
expression elements including a promoter and a ribosome binding site; and fusion partner sequences.

13. An expression vector, comprising: the nucleotide sequence of at least two selected from the group consisting of SEQ ID NO: 01 (Tuf), SEQ ID NO: 02 (NOX), and SEQ ID NO: 03 (MS53-0285)
expression elements including a promoter and a ribosome binding site; and fusion partner sequences.

14. The expression vector of claim 12, wherein said fusion partner is DsbC from *E. coli*, MsyB from *E. coli*, FklB from *E. coli* or a combination thereof.

15. The expression vector of claim 12, wherein said expression vector comprises the has a sequence of SEQ ID NO: 07, SEQ ID NO: 08, or SEQ ID NO: 09.

16. The expression vector of claim 13, wherein said fusion partner is DsbC from *E. coli*, MsyB from *E. coli*, FklB from *E. coli* or a combination thereof.

17. The expression vector of claim 13, wherein said expression vector has a comprises the sequence of SEQ ID NO: 07, SEQ ID NO: 08, or SEQ ID NO: 09.

18. A method for alleviating symptoms caused by *Mycoplasma synoviae infection*, said method comprising:
administering the composition of claim 1 to a subject.

* * * * *

SEQUENCE LISTING

<160> NUMBER OF SEQ ID NOS: 37

<210> SEQ ID NO 1
<211> LENGTH: 394
<212> TYPE: PRT
<213> ORGANISM: Mycoplasma synoviae

<400> SEQUENCE: 1

```
Met Ala Lys Leu Asp Phe Asp Arg Ser Lys Glu His Val Asn Val Gly
  1               5                  10                  15

Thr Ile Gly His Val Asp His Gly Lys Thr Thr Leu Thr Ala Ala Ile
             20                  25                  30

Ala Thr Val Leu Ser Lys Gly Leu Ser Glu Ala Arg Asp Tyr Ala
             35                  40                  45

Ser Ile Asp Asn Ala Pro Glu Glu Lys Ala Arg Gly Ile Thr Ile Asn
 50                  55                  60

Thr Ser His Ile Glu Tyr Gln Thr Glu Lys Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ala Ala Thr Asp Gly Pro
                100                 105                 110

Met Pro Gln Thr Arg Glu His Ile Leu Leu Ser Lys Gln Val Gly Val
             115                 120                 125

Pro Arg Met Val Val Phe Leu Asn Lys Cys Asp Met Val Asp Asp Glu
         130                 135                 140

Glu Met Ile Gly Leu Val Glu Met Glu Ile Arg Asp Leu Leu Ser Glu
145                 150                 155                 160

Tyr Gly Phe Asp Gly Asp Asn Ala Pro Ile Val Arg Gly Ser Ala Leu
                 165                 170                 175

Lys Ala Leu Glu Gly Asp Ala Val Tyr Glu Asp Lys Ile Met Glu Leu
             180                 185                 190

Met Asn Ala Val Asp Thr Tyr Ile Glu Asn Pro Val Lys Glu Leu Asp
         195                 200                 205

Lys Pro Phe Leu Met Ala Val Glu Asp Val Phe Thr Ile Thr Gly Arg
         210                 215                 220

Gly Thr Val Ala Thr Gly Arg Val Glu Arg Gly Arg Leu Thr Leu Asn
225                 230                 235                 240

Glu Glu Val Glu Ile Val Gly Leu Lys Pro Thr Lys Thr Val Val
                 245                 250                 255

Thr Gly Ile Glu Met Phe Arg Lys Asn Leu Lys Glu Ala Leu Ala Gly
             260                 265                 270

Asp Asn Ala Gly Leu Leu Leu Arg Gly Val Asn Arg Asp Asp Val Glu
         275                 280                 285

Arg Gly Gln Val Leu Ala Lys Pro Gly Ser Ile Val Pro His Thr Glu
         290                 295                 300

Phe Glu Ala Ala Ile Tyr Val Leu Lys Lys Glu Glu Gly Gly Arg His
305                 310                 315                 320

Thr Pro Phe Phe Lys Asn Tyr Lys Pro Gln Phe Tyr Phe Arg Thr Thr
             325                 330                 335

Asp Val Thr Gly Gly Val Glu Phe Glu Ala Gly Arg Glu Met Val Met
             340                 345                 350

Pro Gly Glu Asn Val Asn Leu Lys Val Lys Leu Ile Ser Pro Ile Ala
         355                 360                 365

Val Glu Glu Gly Thr Lys Phe Ser Ile Arg Gly Gly Arg Thr Val
         370                 375                 380

Gly Ala Gly Ser Val Thr Lys Ile Val Lys
385                 390

<210> SEQ ID NO 2
<211> LENGTH: 458
```

```
<212> TYPE: PRT
<213> ORGANISM: Mycoplasma synoviae

<400> SEQUENCE: 2

Met Glu Asn Lys Lys Ile Ile Val Val Gly Ala Asn His Ala Gly Thr
1               5                   10                  15

Ser Phe Leu Arg Thr Leu Lys Thr Val Asn Pro Ser Ala Glu Val Val
            20                  25                  30

Ala Tyr Asp Arg Asn Thr Asn Val Ser Phe Leu Gly Cys Gly Ile Ala
        35                  40                  45

Val Trp Val Gly Gly Met Phe Lys Asp Pro Ala Gly Leu Phe Tyr Ser
    50                  55                  60

Ser Pro Glu Val Leu Thr Lys Glu Tyr Gly Val Lys Leu His Thr Gln
65                  70                  75                  80

His Asp Val Val Lys Ile Asp Arg Lys Ser Lys Lys Val Val Val Lys
                85                  90                  95

Asp Leu Gln Thr Gly Arg Glu Phe Glu Asp Ser Tyr Asp Lys Leu Val
            100                 105                 110

Phe Ala Gly Gly Thr Trp Pro Ile Val Pro Pro Phe Lys Gly Lys Asp
        115                 120                 125

Leu Lys Asn Val Leu Leu Ser Lys Leu Phe Gln His Ala Glu Glu Ile
    130                 135                 140

Ile Thr Lys Ala Lys Asp Pro Asn Val Lys Asn Val Val Val Val Gly
145                 150                 155                 160

Ala Gly Tyr Ile Gly Val Glu Leu Val Glu Ala Phe His Val Arg Gly
                165                 170                 175

Lys Asn Val Thr Leu Ile Asp Val Gln Asp Arg Val Val Pro Asn Tyr
            180                 185                 190

Phe Asp Pro Glu Phe Thr Asp Lys Met Glu Glu Asn Met Arg Lys Gly
        195                 200                 205

Gly Val Asn Leu Arg Leu Gly Glu Ser Val Glu Glu Phe Thr Ser Lys
    210                 215                 220

Asp Gly Val His Val Ser Gly Val Lys Thr Asn Lys Gly Ser Tyr Asp
225                 230                 235                 240

Ala Asp Leu Val Leu Leu Cys Ile Gly Phe Arg Pro Gln Thr Ala Val
                245                 250                 255

Val Glu Asp Val Glu Lys Leu Pro Asn Gly Ala Ile Lys Val Asp Glu
            260                 265                 270

Tyr Gln Arg Ser Val Ser Asp Glu Asn Val Tyr Val Ile Gly Asp Ser
        275                 280                 285

Ala Ser Leu Lys Asn Val Ile Thr Asn Asp Tyr Ala His Val Ala Leu
    290                 295                 300

Ala Thr Asn Ala Val Lys Thr Gly Ile Val Ala Ala Leu His Leu Ala
305                 310                 315                 320

Gly Met Asp Val Lys Phe Pro Gly Val Val Gly Thr Asn Ala Val Ser
                325                 330                 335

Val Phe Asp Cys Lys Tyr Ala Ser Thr Gly Phe Thr Lys Arg Leu Gly
            340                 345                 350

Glu Lys Asn Gly Leu Glu Asn Leu Ala Glu Val Tyr Phe Glu Asp Asn
        355                 360                 365

Asp Arg Pro Glu Phe Met Ala His Tyr Glu Lys Ala Ala Cys Lys Ile
    370                 375                 380

Val Tyr Asp Thr Lys Thr Leu Lys Leu Val Gly Ala Gln Val Gly Ser
385                 390                 395                 400
```

```
Trp Gly Gln Asp Ser His Ala Glu Ile Ile Tyr Met Leu Ala Leu Ala
                405                 410                 415

Ile Gln Arg Gly Leu Thr Leu Pro Glu Leu Ala Leu Thr Asp Val Phe
            420                 425                 430

Phe Leu Pro His Phe Asn Lys Pro Phe Asn Phe Val Leu Val Pro Val
        435                 440                 445

Leu Arg Ala Leu Gly Leu Lys Tyr Lys Ala
    450                 455

<210> SEQ ID NO 3
<211> LENGTH: 797
<212> TYPE: PRT
<213> ORGANISM: Mycoplasma synoviae
<400> SEQUENCE: 3

Met Asn Lys Thr Lys Ile Lys Phe Ile Leu Gly Thr Leu Gly Ser Ile
1               5                   10                  15

Ala Ala Leu Ser Ile Ser Ala Ser Cys Gly Ser Ser Asn Gly Ser Ile
            20                  25                  30

Asn Glu Ser Asn Asn Asn Ile Gly Gly Val Thr Asp Asn Ser Ser Ile
        35                  40                  45

Lys Asp Arg Arg Leu Asn Ala Leu Leu Gly Ala Asn Pro Glu Ala Ser
    50                  55                  60

Ser Asn Ala Phe Gln Gln Val Glu Lys Asp Lys Ile Val Leu Ala Met
65                  70                  75                  80

Thr Phe Ser Gln Gly Gly Ala Gln Ala Lys Ala Leu Asn Glu Leu Val
                85                  90                  95

Asn Ala Tyr Asn Asn Asp Ala Glu Leu Lys Ala Lys Leu Gly Asn Ile
            100                 105                 110

Phe Lys Glu Val Thr Val Asn Asn Val Gly Ser Gly Tyr Gly Glu Gly
        115                 120                 125

Ala Lys Lys Val Ser Gln Tyr Leu Glu Ala Lys Asn Thr Asp Asn Phe
    130                 135                 140

Phe Asn Leu Ile Leu Asn Tyr Ser Pro Val Gly Ala Ile Leu Ala Asn
145                 150                 155                 160

Ser Asn Met Leu Leu Ser Phe Asn Asp Pro Asn Gly Asn Pro Asp Leu
                165                 170                 175

Asp Thr Asp Ile Ser Leu Phe Asn Lys Asp Phe Val Asn Ser Asn Ala
            180                 185                 190

Thr Thr Glu Asn Ile Lys Asn Pro Ser Thr Tyr Ile Leu Pro Ile Met
        195                 200                 205

Lys Ser Thr Leu Val Ser Thr Ile Asn Ala Pro Val Met Ser Tyr Ile
    210                 215                 220

Leu Asp Thr Met Lys Ala Lys Gly Val Thr Phe Ser Asp Asp Val Asp
225                 230                 235                 240

Thr Lys Asn Phe Val Ala Glu Ile Asp Ser Lys Gly Gln Pro Asp Arg
                245                 250                 255

Ser Gln Ile Gln Lys Gln Trp Gly Asp Pro Val Asp Asn Ala Thr Glu
            260                 265                 270

Leu Leu Lys Gly Phe Gln Phe Ser Lys Lys Ile Phe Asn Asn Tyr Glu
        275                 280                 285

Asp Leu Ile Lys Phe Ala Glu Leu Ala Gln Lys Leu Phe Lys Asn Thr
    290                 295                 300

Gln Asp Asn Gln Asn Asp Leu His Val Leu Gly Ile Asp Ser Pro Thr
```

```
305                 310                 315                 320
Ser Thr Phe Gln Asn Ser Val Tyr Ser Leu Thr Gly Tyr Arg Tyr Ala
                325                 330                 335
Asn Ser Leu Glu Ala Thr Ser Lys Lys Asn Gly Val Asn Thr Val Asn
                340                 345                 350
Tyr Asn Ser Leu Thr Thr Thr Gly Ser Pro Ala Asn Val Ala Ala Lys
                355                 360                 365
Thr Val Tyr Glu Thr Phe Arg Ser Ala Val Ala Thr Gln Gly Val Val
    370                 375                 380
Leu Gln Gly Pro Gly Gln Phe Thr Ser Asn Lys Gln Ile Tyr His Lys
385                 390                 395                 400
Phe Ala Met Ser Ile Gly Ser Ile Ala Gly Tyr Thr His Asn Tyr Ile
                405                 410                 415
Glu Ser Val Glu Gly Thr Ile Asn Phe Asn Phe Ser Gln Tyr Ser Gly
                420                 425                 430
Phe Asn Phe Lys Ala Ser Thr Asn Lys Ser Asp Arg Asn Asn Tyr Asn
                435                 440                 445
Arg Ser Gly Phe Leu Thr Phe Gly Leu Gly Leu Asn Gly Leu Gly Arg
    450                 455                 460
Lys Tyr Arg Thr Asn Tyr Thr Ser Asp Gln Ile Phe Leu Gly Phe Gly
465                 470                 475                 480
Ser Phe Lys Asn Gly Leu Ala Lys Ser Asn Val Thr Leu Lys Ser Arg
                485                 490                 495
Phe Asp Ile Lys Ser Ile Asp Thr Thr Asn Asp Ala Ser Ile Gln Ala
                500                 505                 510
Ala Ile Asp Lys Ile Lys Asn Asp Thr Ser Asn Trp Lys Leu Leu Leu
                515                 520                 525
Leu Gln Gln Ser Asp Ser Ser Lys Thr Gln Glu Phe Thr Asp Phe Gln
                530                 535                 540
Thr Val Val Lys Asn Ala Ala Ser Gln Asn Ser Ser Glu Ile Ile Tyr
545                 550                 555                 560
Gly Gly Val Ala Glu Ser Ser Asn Ser Lys Asn Pro Gln Lys Ser Leu
                565                 570                 575
Val Val Phe Val Lys Ser Ser Asn Ser Asn Pro Val Lys Ala Asp Trp
                580                 585                 590
Glu Lys Tyr Ile Lys Leu Leu Gly Gly Thr Ala Glu Glu Gln Thr Ser
                595                 600                 605
Ser Asn Thr Leu Asn Lys Asn Glu Leu Val Val Ile Asn Ala Pro Thr
                610                 615                 620
Lys Trp Asn Glu Asn Ser Ala Lys Asn Ser Ile Tyr Leu Gln Gly Pro
625                 630                 635                 640
Ser Leu Ile Gly Ile Lys Ala Asn Glu Val Asp Ala Ala Thr Arg
                645                 650                 655
Ala Phe Val His Trp Leu Val Thr Ser Lys Lys Glu Tyr Thr Phe Phe
                660                 665                 670
Lys Asp Asp Ser Lys Ser Thr Val Thr Ala Thr Pro Ser Leu Phe Phe
                675                 680                 685
Gln Lys Gln Met Ser Tyr Val Met Pro Thr Ser Asp Phe Gln Asn Ser
                690                 695                 700
Val Ser Asp Lys Thr Phe Asp Ser Gly Lys Asn Ser Arg Thr Asp Asn
705                 710                 715                 720
Pro Phe Leu Glu Asn Ala Leu Gln Val Phe Lys Asn Ala Ala Lys Asp
                725                 730                 735
```

```
Gln Ala Asn Trp Thr Thr Tyr Glu Ser Pro Gly Ser Glu Lys Gly Asp
                740                 745                 750

Ala Phe Arg Asn Ser Val Glu Ser Ala Phe Lys Asn Leu Ile Asn Gln
            755                 760                 765

Ala Ala Asn Gly Thr Gln Val Ser Gln Leu Gln Thr Phe Asp Gln Phe
        770                 775                 780

Val Gln Ser Phe Arg Asp Thr Phe Gly Ser Asn Asn Asn
785                 790                 795
```

<210> SEQ ID NO 4
<211> LENGTH: 1182
<212> TYPE: DNA
<213> ORGANISM: Artificial Sequence
<220> FEATURE:
<223> OTHER INFORMATION: mutant Tuf

<400> SEQUENCE: 4

```
atggcaaaat tagattttga ccgttcaaaa gaacacgtta acgttggaac cattggacac      60
gttgaccacg gtaaaccac tcttacagct gctattgcaa ctgttttatc taaaaaggga     120
ttatcagaag ctcgtgatta tgcttctatt gataatgcac ctgaagaaaa agctcgtggt     180
ataaccatta atacttcaca cattgagtac caaacagaaa acgtcacta tgctcacgtt     240
gactgtccag tcacgctga ctacgttaaa aacatgatta caggggctgc acaaatggat     300
ggtgctattc ttgttgttgc tgcaacagat gggcctatgc ctcaaactcg tgaacacatt     360
cttctttcaa acaagttgg tgttccaaga atggtggttt tcctaaacaa atgtgacatg     420
gttgatgacg aagaaatgat tgggcttgtt gaaatggaaa ttcgtgatct attatcagaa     480
tacggatttg acggagacaa cgctcctatc gttagaggat cagctcttaa agcacttgaa     540
ggtgacgcag tatatgaaga caaaattatg gaattaatga atgctgttga cacatacatt     600
gaaaacccag ttaaagaact agacaaacca ttcttaatgg ctgttgaaga cgttttcaca     660
attacaggac gtggaactgt tgctacagga cgtgtagaac gtggaagatt aacacttaac     720
gaagaagttg aaattgttgg tctaaaacct accaagaaaa ctgttgttac aggaatcgaa     780
atgtttagaa aaacctaaa agaagctcta gctggagata cgctggatt gcttcttcgt     840
ggagttaacc gtgatgacgt agaacgtgga caagttcttg caaaaccagg atcaatcgtt     900
cctcacacag aattcgaagc tgcaatttat gttcttaaaa agaagaagg tggacgtcac     960
acaccattct ttaaaaacta taaacctcaa ttctacttcc gtacaacaga cgttacaggt    1020
ggagttgaat tcgaagctgg acgtgaaatg gttatgccag tgaaaacgt taacttaaaa    1080
gttaaattaa tttcaccaat cgctgttgaa gaaggaacca aattctctat ccgtgaaggt    1140
ggaagaactg ttggtgccgg atcagttaca aaaatcgtta aa                      1182
```

<210> SEQ ID NO 5
<211> LENGTH: 1374
<212> TYPE: DNA
<213> ORGANISM: Artificial Sequence
<220> FEATURE:
<223> OTHER INFORMATION: mutant NOX

<400> SEQUENCE: 5

```
atggaaaaca aaaaaattat agttgttggt gcaaatcacg ccggaacttc attttttaaga     60
acttaaaaa cagtaaatcc atcagctgaa gttgtagctt atgatagaaa tacaaacgta    120
tcatttttag gatgtggtat tgctgtttgg ggttggagga atgtttaaga tccagctgga    180
```

```
ttattttatt catctccaga agttttaaca aaagaatacg gagttaaact tcacacacaa    240
cacgacgttg taaaaatcga tagaaaaagc aaaaaagttg ttgttaaaga tttacaaaca    300
ggcagagaat tcgaagattc atacgataag ttagtttttg ctggaggaac atggcctata    360
gttcctccat ttaaaggtaa agacttaaaa aatgttttac tttctaagtt attccaacat    420
gctgaggaaa taatcaccaa agcaaaagat ccaaacgtta aaaacgtagt agttgttgga    480
gcaggatata ttggtgttga gctggttgaa gctttccacg ttagaggaaa aaatgttact    540
ctaatcgacg ttcaagatag agttgttcct aactattttg atcctgaatt tacagacaaa    600
atggaagaaa acatgcgtaa aggtggagtt aatcttcgtc ttggtgaaag tgttgaagaa    660
tttacttcaa aagatggtgt gcatgtttct ggggttaaaa ccaacaaagg tagctatgac    720
gctgatttag tgcttctttg catcggattt agaccacaaa ctgcagttgt tgaagatgtt    780
gaaaaacttc caaatggagc aattaaagtt gacgaatacc aaagatcagt ttcagatgaa    840
aacgtttatg taattggtga ttcagcttct cttaaaaacg taattacaaa cgactatgct    900
cacgtagctt tagctacaaa cgcagttaaa accggaatcg tagcagctct gcaccttgct    960
ggaatggatg ttaaattccc aggagttgtt ggaactaatg ctgttagcgt atttgactgt   1020
aaatatgcat caactggatt tacaaaaaga ttaggtgaaa aaaatggcct tgaaaactta   1080
gctgaggttt attttgaaga taatgatcgt ccagaattta tggctcacta tgaaaaagcg   1140
gcatgtaaaa tcgtatacga tacaaaaaca cttaaattag ttggagctca agttggttct   1200
tggggacaag attctcatgc tgaaattatt tatatgctag ctcttgcaat tcaaagagga   1260
cttactcttc ctgaacttgc attaactgat gtattttcc ttcctcactt taacaaacca   1320
tttaactttg ttttagttcc agttttaaga gcacttggtt taaaatataa agct          1374

<210> SEQ ID NO 6
<211> LENGTH: 2391
<212> TYPE: DNA
<213> ORGANISM: Artificial Sequence
<220> FEATURE:
<223> OTHER INFORMATION: mutant MS53

<400> SEQUENCE: 6
atgaataaaa caaaaattaa atttatttta ggaacgctag gttcaattgc agcgttatct     60
atttctgcat catgtggaag ttcaaatgga tcaataaatg aaagtaacaa taatattggc    120
ggtgttactg acaattcatc tatcaaagat agaagattaa acgctttatt aggcgcaaat    180
ccagaagcat cttctaacgc ttttcagcaa gttgaaaaag acaaaattgt tttagctatg    240 acttttttcac aaggggagc acaagcaaaa gctttaaatg aattagttaa tgcttataat    300
aatgatgccg aattaaaagc gaaacttgga atattttca agaagttac tgtaaataat    360 gttggttcag ttatgggga aggagcaaaa aaagtatcgc aatatttaga agctaaaaat    420
actgataatt ttttaacttt aattttaaat tattctcctg ttggggcaat acttgcaaat    480
agcaatatgt tattaagttt taacgaccca aatggaaatc ctgatttaga tacagatatt    540
tcattattta caaggatttt tgttaattca aacgcaacaa cagaaaacat taaaaaccca    600 tctcatataca tattaccaat aatgaaaagt actttggttt caactattaa tgctcctgtt    660
atgtcttata tattagacac aatgaaagca aaggagtaa cttttctcaga tgatgttgat    720 acaaaaaatt ttgttgcaga aatagattct aagggtcaac ctgacagaag tcaaattcaa    780
aagcaatggg gtgatccagt cgataacgca actgaattat taaaaggctt tcaatttttct    840 aaaaagattt ttaataatta tgaagattta attaaattg ctgaattagc acaaaaatta    900
```

```
tttaaaaata cacaagataa tcaaaatgat ttacacgttt taggtattga cagccctaca      960
tcaacattcc aaaatagtgt ttattcatta actggatatc ggtatgctaa ttctcttgaa     1020
gcaacttcta aaaaaatgg agtaaatact gttaattata attctttaac aacaacaggt     1080
tctccagcta atgttgcagc aaaaactgtt tatgaaacat ttagaagcgc agttgcaaca     1140
cagggtgtgg tattacaagg tccaggacaa tttacttcaa ataaacaaat ttatcataaa     1200
tttgcaatga gtattggttc aattgctggt tatactcaca actatattga atcagttgag     1260
ggaacaatta atttaatttt ctctcaatat tctggtttca actttaaagc ttcaacaaat     1320
aaaagcgata gaaataacta taatagatca ggattttaa catttggatt aggacttaat     1380
ggtcttggaa gaaaatatag aacaaattat acaagtgatc aaatattttt aggatttggt     1440
tcatttaaaa atggtcttgc aaaatcaaat gttactttaa aatcacgttt tgatattaag     1500
tcaatagaca caacaaacga tgcatcaatt caagctgcta tagataaaat taaaaacgat     1560
acaagtaatt ggaaattatt gttattgcaa caagtgata gttcaaaaac tcaagaattt     1620
acagatttcc aaacagtggt aaagaatgca gctagtcaaa attcaagtga aattatttat     1680
ggtggagttg ctgaaagtag caattctaaa aacccacaaa aaagtcttgt tgtatttgtg     1740
aaaagttcaa attcaaatcc agttaaagct gattgggaaa aatatattaa attactaggt     1800
ggaactgctg aagaacaaac ttcatcaaat acattaaata aaaatgaact tgtagtaata     1860
aatgctccaa caaaatggaa tgaaaattca gcaaaaaatt caattttattt acaaggtcct     1920
agtttaattg gtataaaagc aaatgaagtt gatgatgctg ctactagagc atttgtacat     1980
tggcttgtaa cttctaagaa agaatatact ttcttaaag atgattcaaa atcaacagta     2040
actgcaactc cttcattatt tttccaaaaa caaatgtcat atgtaatgcc aacatcagat     2100
tttcaaaatt cagtttctga taaacatttt gattctgaa aaaattcaag aacagataac     2160
ccattcttag aaaatgcatt acaagtattt aaaaatgcag caaaagatca agcaaactgg     2220
actacatatg aatcaccagg ttcagaaaaa ggtgatgcat ttagaaattc tgttgaatca     2280
gcatttaaaa atttaataaa tcaagctgca aatggaacac aagtttcaca acttcaaaca     2340
tttgatcaat ttgttcaatc atttagagat acatttggtt caaataataa t              2391
```

<210> SEQ ID NO 7
<211> LENGTH: 7116
<212> TYPE: DNA
<213> ORGANISM: Artificial Sequence
<220> FEATURE:
<223> OTHER INFORMATION: plasmid

<400> SEQUENCE: 7

```
atccggatat agttcctcct ttcagcaaaa aaccccctcaa gacccgttta gaggccccaa       60
ggggttatgc tagttattgc tcagcggtgg cagcagccaa ctcagcttcc tttcgggctt      120
tgttagcagc cggatctcag tggtggtggt ggtggtgctc gagtgcggcc gcaagcttgt      180
cgactttaac gattttgta actgatccgg caccaacagt tcttccacct tcacggatag      240
agaatttggt tccttcttca acagcgattg gtgaaattaa tttaactttt aagttaacgt      300
tttcacctgg cataaccatt tcacgtccag cttcgaattc aactccacct gtaacgtctg      360
ttgtacggaa gtagaattga ggtttatagt ttttaaagaa tggtgtgtga cgtccacctt      420
cttctttttt aagaacataa attgcagctt cgaattctgt gtgaggaacg attgatcctg      480
gttttgcaag aacttgtcca cgttctacgt catcacggtt aactccacga agaagcaatc      540
```

-continued

```
cagcgttatc tccagctaga gcttctttta ggttttttct aaacatttcg attcctgtaa    600
caacagtttt cttggtaggt tttagaccaa caatttcaac ttcttcgtta agtgttaatc    660
ttccacgttc tacacgtcct gtagcaacag ttccacgtcc tgtaattgtg aaaacgtctt    720
caacagccat taagaatggt ttgtctagtt ctttaactgg gttttcaatg tatgtgtcaa    780
cagcattcat taattccata attttgtctt catatactgc gtcaccttca agtgctttaa    840
gagctgatcc tctaacgata ggagcgttgt ctccgtcaaa tccgtattct gataatagat    900
cacgaatttc catttcaaca agcccaatca tttcttcgtc atcaaccatg tcacatttgt    960
ttaggaaaac caccattctt ggaacaccaa cttgttttga agaagaatg tgttcacgag    1020
tttgaggcat aggcccatct gttgcagcaa caacaagaat agcaccatcc atttgtgcag    1080
cccctgtaat catgttttta acgtagtcag cgtgacctgg acagtcaacg tgagcatagt    1140
gacgttttc tgtttggtac tcaatgtgtg aagtattaat ggttatacca cgagcttttt    1200
cttcaggtgc attatcaata gaagcataat cacgagcttc tgataatccc tttttagata    1260
aaacagttgc aatagcagct gtaagagtgg ttttaccgtg gtcaacgtgt ccaatggttc    1320
caacgttaac gtgttctttt gaacggtcaa aatctaattt tgccatggat cctttaccgc    1380
tggtcatttt ttggtgttcg tcgaggaatt cttttcatctc tttcggcggc tggtaacccg    1440
gaacaagtgt gccattgctc agcacaactg ccggagtacc gctaacgcca agctggacgc    1500
caagtgcgta atggtcggca atatccacgt cgcaactggc tggtgcgacg cttttacctg    1560
ccatcacatc atcaaacgct ttgtttttat ctttcgcaca ccagatagct ttcatttctt    1620
tctctgcatc gctgtccagc ccctggcgcg ggaaagcaag ataacgcacg gtgatcccca    1680
gcgcgttgta gtctgccatt tgctcatgca gtttgtggca gtaaccacag gtaatatcag    1740
taaacacggt gatgacgtgt ttttcctgcg gcgctttata aacgatcatc tcttttcaa    1800
gcgcattcaa ctgctttaac agcatcttat tggtgacatt gaccggagcc gtgccactaa    1860
cgtcatacat tggcccctga atgatatgtt taccatcatc ggtgatgtac aacacgccgc    1920
tgttagtcag aactgtcttc atgccagcta caggcgcggg ctgaatatcg ctgcttttga    1980
tgcccatttt ggctaacgtt tgttgaattg ccgcgtcatc gtgatggtga tggtgatgca    2040
tatgtatatc tccttcttaa agttaaacaa aattatttct agaggggaat tgttatccgc    2100
tcacaattcc cctatagtga gtcgtattaa tttcgcggga tcgagatcga tctcgatcct    2160
ctacgccgga cgcatcgtgg ccggcatcac cggcgccaca ggtgcggttg ctggcgccta    2220
tatcgccgac atcaccgatg gggaagatcg ggctcgccac ttcgggctca tgagcgcttg    2280
tttcggcgtg gtatggtgg caggccccgt ggccggggga ctgttgggcg ccatctcctt    2340
gcatgcacca ttccttgcgg cggcggtgct caacggcctc aacctactac tgggctgctt    2400
cctaatgcag gagtcgcata agggagagcg tcgagatccc ggacaccatc gaatggcgca    2460
aaacctttcg cggtatggca tgatagcgcc cggaagagag tcaattcagg gtggtgaatg    2520
tgaaaccagt aacgttatac gatgtcgcag agtatgccgg tgtctcttat cagaccgttt    2580
cccgcgtggt gaaccaggcc agccacgttt ctgcgaaaac gcgggaaaaa gtggaagcgg    2640
cgatggcgga gctgaattac attcccaacc gcgtggcaca caactggcg ggcaaacagt    2700
cgttgctgat tggcgttgcc acctccagtc tggccctgca cgcgccgtcg caaattgtcg    2760
cggcgattaa atctcgcgcc gatcaactgg gtgccagcgt ggtggtgtcg atggtagaac    2820
gaagcggcgt cgaagcctgt aaagcggcgg tgcacaatct tctcgcgcaa cgcgtcagtg    2880
ggctgatcat taactatccg ctggatgacc aggatgccat tgctgtggaa gctgcctgca    2940
```

```
ctaatgttcc ggcgttattt cttgatgtct ctgaccagac acccatcaac agtattattt   3000
tctcccatga agacggtacg cgactgggcg tggagcatct ggtcgcattg ggtcaccagc   3060
aaatcgcgct gttagcgggc ccattaagtt ctgtctcggc gcgtctgcgt ctggctggct   3120
ggcataaata tctcactcgc aatcaaattc agccgatagc ggaacgggaa ggcgactgga   3180
gtgccatgtc cggttttcaa caaccatgc aaatgctgaa tgagggcatc gttcccactg    3240
cgatgctggt tgccaacgat cagatggcgc tgggcgcaat gcgcgccatt accgagtccg   3300
ggctgcgcgt tggtgcggac atctcggtag tgggatacga cgataccgaa gacagctcat   3360
gttatatccc gccgttaacc accatcaaac aggattttcg cctgctgggg caaaccagcg   3420
tggaccgctt gctgcaactc tctcagggcc aggcggtgaa gggcaatcag ctgttgcccg   3480
tctcactggt gaaaagaaaa accaccctgg cgcccaatac gcaaaccgcc tctccccgcg   3540
cgttggccga ttcattaatg cagctggcac gacaggtttc ccgactggaa agcgggcagt   3600
gagcgcaacg caattaatgt aagttagctc actcattagg caccgggatc tcgaccgatg   3660
cccttgagag ccttcaaccc agtcagctcc ttccggtggg cgcggggcat gactatcgtc   3720
gccgcactta tgactgtctt ctttatcatg caactcgtag acaggtgcc ggcagcgctc    3780 tgggtcattt tcggcgagga ccgctttcgc tggagcgcga cgatgatcgg cctgtcgctt   3840
gcggtattcg gaatcttgca cgccctcgct caagccttcg tcactggtcc cgccaccaaa   3900
cgtttcggcg agaagcaggc cattatcgcc ggcatggcgg ccccacgggt gcgcatgatc   3960
gtgctcctgt cgttgaggac ccggctaggc tggcggggtt gccttactgg ttagcagaat   4020
gaatcaccga tacgcgagcg aacgtgaagc gactgctgct gcaaaacgtc tgcgacctga   4080
gcaacaacat gaatggtctt cggtttccgt gtttcgtaaa gtctggaaac gcggaagtca   4140
gcgccctgca ccattatgtt ccggatctgc atcgcaggat gctgctggct accctgtgga   4200
acacctacat ctgtattaac gaagcgctgg cattgaccct gagtgatttt tctctggtcc   4260
cgccgcatcc ataccgccag ttgtttaccc tcacaacgtt ccagtaaccg gcatgttca    4320 tcatcagtaa cccgtatcgt gagcatcctc tctcgtttca tcggtatcat taccccatg    4380 aacagaaatc cccc ttacac ggaggcatca gtgaccaaac aggaaaaaac cgcccttaac   4440
atggcccgct ttatcagaag ccagacatta acgcttctgg agaaactcaa cgagctggac   4500
gcggatgaac aggcagacat ctgtgaatcg cttcacgacc acgctgatga gctttaccgc   4560
agctgcctcg cgcgtttcgg tgatgacggt gaaaacctct gacacatgca gctcccggag   4620
acggtcacag cttgtctgta agcggatgcc gggagcagac aagcccgtca gggcgcgtca   4680
gcgggtgttg gcgggtgtcg ggcgcagcc atgacccagt cacgtagcga tagcggagtg    4740
tatactggct taactatgcg gcatcagagc agattgtact gagagtgcac catatatgcg   4800
gtgtgaaata ccgcacagat gcgtaaggag aaaataccgc atcaggcgct cttccgcttc   4860
ctcgctcact gactcgctgc gctcggtcgt tcggctgcgg cgagcggtat cagctcactc   4920
aaaggcggta atacggttat ccacagaatc aggggataac gcaggaaaga acatgtgagc   4980
aaaaggccag caaaaggcca ggaaccgtaa aaaggccgcg ttgctggcgt ttttccatag   5040
gctccgcccc cctgacgagc atcacaaaaa tcgacgctca agtcagaggt ggcgaaaccc   5100
gacaggacta taaagatacc aggcgtttcc ccctggaagc tccctcgtgc gctctcctgt   5160
tccgaccctg ccgcttaccg gatacctgtc cgcctttctc ccttcgggaa gcgtggcgct   5220
ttctcatagc tcacgctgta ggtatctcag ttcggtgtag gtcgttcgct ccaagctggg   5280
```

```
ctgtgtgcac gaaccccccg ttcagcccga ccgctgcgcc ttatccggta actatcgtct    5340
tgagtccaac ccggtaagac acgacttatc gccactggca gcagccactg gtaacaggat    5400
tagcagagcg aggtatgtag gcggtgctac agagttcttg aagtggtggc ctaactacgg    5460
ctacactaga aggacagtat ttggtatctg cgctctgctg aagccagtta ccttcggaaa    5520
aagagttggt agctcttgat ccggcaaaca aaccaccgct ggtagcggtg ttttttttgt    5580
ttgcaagcag cagattacgc gcagaaaaaa aggatctcaa gaagatcctt tgatcttttc    5640
tacggggtct gacgctcagt ggaacgaaaa ctcacgttaa gggattttgg tcatgaacaa    5700
taaaactgtc tgcttacata acagtaata caagggggtgt tatgagccat attcaacggg    5760
aaacgtcttg ctctaggccg cgattaaatt ccaacatgga tgctgattta tatgggtata    5820
aatgggctcg cgataatgtc gggcaatcag gtgcgacaat ctatcgattg tatgggaagc    5880
ccgatgcgcc agagttgttt ctgaaacatg gcaaaggtag cgttgccaat gatgttacag    5940
atgagatggt cagactaaac tggctgacgg aatttatgcc tcttccgacc atcaagcatt    6000
ttatccgtac tcctgatgat gcatggttac tcaccactgc gatccccggg aaaacagcat    6060
tccaggtatt agaagaatat cctgattcag gtgaaaatat tgttgatgcg ctggcagtgt    6120
tcctgcgccg gttgcattcg attcctgttt gtaattgtcc ttttaacagc gatcgcgtat    6180
ttcgtctcgc tcaggcgcaa tcacgaatga ataacggttt ggttgatgcg agtgattttg    6240
atgacgagcg taatggctgg cctgttgaac aagtctggaa agaaatgcat aaacttttgc    6300
cattctcacc ggattcagtc gtcactcatg gtgatttctc acttgataac cttatttttg    6360
acgaggggaa attaataggt tgtattgatg ttggacgagt cggaatcgca gaccgatacc    6420
aggatcttgc catcctatgg aactgcctcg gtgagttttc tccttcatta cagaaacggc    6480
tttttcaaaa atatggtatt gataatcctg atatgaataa attgcagttt catttgatgc    6540
tcgatgagtt tttctaagaa ttaattcatg agcggataca tatttgaatg tatttagaaa    6600
aataaacaaa taggggttcc gcgcacattt ccccgaaaag tgccacctga aattgtaaac    6660
gttaatattt tgttaaaatt cgcgttaaat ttttgttaaa tcagctcatt ttttaaccaa    6720
taggccgaaa tcggcaaaat cccttataaa tcaaaagaat agaccgagat agggttgagt    6780
gttgttccag tttggaacaa gagtccacta ttaaagaacg tggactccaa cgtcaaaggg    6840
cgaaaaaccg tctatcaggg cgatggccca ctacgtgaac catcacccta atcaagtttt    6900
ttggggtcga ggtgccgtaa agcactaaat cggaacccta agggagcccc cgatttaga    6960 gcttgacggg gaaagccggc gaacgtggcg agaaaggaag ggaagaaagc gaaaggagcg    7020
ggcgctaggg cgctggcaag tgtagcggtc acgctgcgcg taaccaccac acccgccgcg    7080
cttaatgcgc cgctacaggg cgcgtcccat tcgcca                              7116
```

<210> SEQ ID NO 8
<211> LENGTH: 7350
<212> TYPE: DNA
<213> ORGANISM: Artificial Sequence
<220> FEATURE:
<223> OTHER INFORMATION: plasmid

<400> SEQUENCE: 8

```
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacagcttt atattttaaa ccaagtgctc ttaaaactgg aactaaaaca aagttaaatg     240
```

```
gtttgttaaa gtgaggaagg aaaaatacat cagttaatgc aagttcagga agagtaagtc      300
ctctttgaat tgcaagagct agcatataaa taatttcagc atgagaatct tgtccccaag      360
aaccaacttg agctccaact aatttaagtg tttttgtatc gtatacgatt ttacatgccg      420 cttttcata gtgagccata aattctggac gatcattatc ttcaaaataa acctcagcta       480
agttttcaag gccatttttt tcacctaatc tttttgtaaa tccagttgat gcatatttac      540
agtcaaatac gctaacagca ttagttccaa caactcctgg gaatttaaca tccattccag      600
caaggtgcag agctgctacg attccggttt taactgcgtt tgtagctaaa gctacgtgag      660
catagtcgtt tgtaattacg tttttaagag aagctgaatc accaattaca taaacgtttt      720
catctgaaac tgatctttgg tattcgtcaa ctttaattgc tccatttgga agttttcaa      780 catcttcaac aactgcagtt tgtggtctaa atccgatgca aagaagcact aaatcagcgt      840
catagctacc tttgttggtt ttaaccccag aaacatgcac accatctttt gaagtaaatt      900
cttcaacact ttcaccaaga cgaagattaa ctccacctttt acgcatgttt tcttccatttt    960 tgtctgtaaa ttcaggatca aaatagttag gaacaactct atcttgaacg tcgattagag     1020
taacattttt tcctctaacg tggaaagctt caaccagctc aacaccaata tatcctgctc     1080
caacaactac tacgttttta acgtttggat cttttgcttt ggtgattatt tcctcagcat     1140
gttggaataa cttagaaagt aaaacatttt ttaagtcttt acctttaaat ggaggaacta    1200
taggccatgt tcctccagca aaaactaact tatcgtatga atcttcgaat tctctgcctg     1260
tttgtaaatc tttaacaaca acttttttgc tttttctatc gattttaca acgtcgtgtt      1320 gtgtgtgaag tttaactccg tattcttttg ttaaaacttc tggagatgaa taaaataatc     1380
cagctggatc tttaaacatt cctccaaccc aaacagcaat accacatcct aaaaatgata     1440
cgtttgtatt tctatcataa gctacaactt cagctgatgg atttactgtt tttaaggttc     1500
ttaaaaatga agttccggcg tgatttgcac caacaactat aattttttg ttttccatgg      1560 atcctttacc gctggtcatt ttttggtgtt cgtcgaggaa ttctttcatc tctttcggcg     1620
gctggtaacc cggaacaagt gtgccattgc tcagcacaac tgccggagta ccgctaacgc     1680
caagctggac gccaagtgcg taatggtcgg caatatccac gtcgcaactg gctggtgcga     1740
cgcttttacc tgccatcaca tcatcaaacg ctttgttttt atctttcgca caccagatag     1800 cttttcatttc tttctctgca tcgctgtcca gcccctggcg cgggaaagca agataacgca     1860
cggtgatccc cagcgcgttg tagtctgcca tttgctcatg cagtttgtgg cagtaaccac     1920
aggtaatatc agtaaacacg gtgatgacgt gtttttcctg cggcgcttta taaacgatca     1980
tctctttttc aagcgcattc aactgcttta acagcatctt attggtgaca ttgaccggag     2040
ccgtgccact aacgtcatac attggcccct gaatgatatg tttaccatca tcggtgatgt     2100
acaacacgcc gctgttagtc agaactgtct tcatgccagc tacaggcgcg ggctgaatat     2160
cgctgctttt gatgcccatt ttggctaacg tttgttgaat tgccgcgtca tcggtaccca     2220
gatctgggct gtccatgtgc tggcgttcga atttagcagc agcggtttct ttcatatgta     2280
tatctccttc ttaaagttaa acaaaattat ttctagaggg gaattgttat ccgctcacaa     2340
ttcccctata gtgagtcgta ttaatttcgc gggatcgaga tcgatctcga tcctctacgc     2400
cggacgcatc gtggccggca tcaccggcgc cacaggtgcg gttgctggcg cctatatcgc     2460
cgacatcacc gatggggaag atcgggctcg ccacttcggg ctcatgagcg cttgtttcgg     2520
cgtgggtatg gtggcaggcc ccgtggccgg gggactgttg ggcgccatct ccttgcatgc     2580
```

```
accattcctt gcggcggcgg tgctcaacgg cctcaaccta ctactgggct gcttcctaat    2640
gcaggagtcg cataagggag agcgtcgaga tcccggacac catcgaatgg cgcaaaacct    2700
ttcgcggtat ggcatgatag cgcccggaag agagtcaatt cagggtggtg aatgtgaaac    2760
cagtaacgtt atacgatgtc gcagagtatg ccggtgtctc ttatcagacc gtttcccgcg    2820
tggtgaacca ggccagccac gtttctgcga aaacgcggga aaaagtggaa gcggcgatgg    2880
cggagctgaa ttacattccc aaccgcgtgg cacaacaact ggcgggcaaa cagtcgttgc    2940
tgattggcgt tgccacctcc agtctggccc tgcacgcgcc gtcgcaaatt gtcgcggcga    3000
ttaaatctcg cgccgatcaa ctgggtgcca gcgtggtggt gtcgatggta gaacgaagcg    3060
gcgtcgaagc ctgtaaagcg gcggtgcaca atcttctcgc gcaacgcgtc agtgggctga    3120
tcattaacta tccgctggat gaccaggatg ccattgctgt ggaagctgcc tgcactaatg    3180
ttccggcgtt atttcttgat gtctctgacc agacacccat caacagtatt attttctccc    3240
atgaagacgg tacgcgactg ggcgtggagc atctggtcgc attgggtcac cagcaaatcg    3300
cgctgttagc gggcccatta agttctgtct cggcgcgtct gcgtctggct ggctggcata    3360
aatatctcac tcgcaatcaa attcagccga tagcggaacg ggaaggcgac tggagtgcca    3420
tgtccggttt tcaacaaacc atgcaaatgc tgaatgaggg catcgttccc actgcgatgc    3480
tggttgccaa cgatcagatg gcgctgggcg caatgcgcgc cattaccgag tccgggctgc    3540
gcgttggtgc ggacatctcg gtagtgggat acgacgatac cgaagacagc tcatgttata    3600
tcccgccgtt aaccaccatc aaacaggatt ttcgcctgct ggggcaaacc agcgtggacc    3660
gcttgctgca actctctcag ggccaggcgg tgaaggcaa tcagctgttg cccgtctcac    3720
tggtgaaaag aaaaaccacc ctggcgccca atacgcaaac cgcctctccc cgcgcgttgg    3780
ccgattcatt aatgcagctg gcacgacagg tttcccgact ggaaagcggg cagtgagcgc    3840
aacgcaatta atgtaagtta gctcactcat taggcaccgg gatctcgacc gatgcccttg    3900
agagccttca acccagtcag ctccttccgg tgggcgcggg gcatgactat cgtcgccgca    3960
cttatgactg tcttctttat catgcaactc gtaggacagg tgccggcagc gctctgggtc    4020
attttcggcg aggaccgctt tcgctggagc gcgacgatga tcggcctgtc gcttgcggta    4080
ttcggaatct tgcacgccct cgctcaagcc ttcgtcactg gtcccgccac caaacgtttc    4140
ggcgagaagc aggccattat cgccggcatg gcggccccac gggtgcgcat gatcgtgctc    4200
ctgtcgttga ggacccggct aggctggcgg ggttgcctta ctggttagca gaatgaatca    4260
ccgatacgcg agcgaacgtg aagcgactgc tgctgcaaaa cgtctgcgac ctgagcaaca    4320
acatgaatgg tcttcggttt ccgtgtttcg taaagtctgg aaacgcggaa gtcagcgccc    4380
tgcaccatta tgttccggat ctgcatcgca ggatgctgct ggctaccctg tggaacacct    4440
acatctgtat taacgaagcg ctggcattga ccctgagtga ttttctctg gtcccgccgc     4500
atccataccg ccagttgttt accctcacaa cgttccagta accgggcatg ttcatcatca    4560
gtaacccgta tcgtgagcat cctctctcgt ttcatcggta tcattacccc catgaacaga    4620
aatccccctt acacggaggc atcagtgacc aaacaggaaa aaaccgccct taacatggcc    4680
cgctttatca gaagccagac attaacgctt ctggagaaac tcaacgagct ggacgcggat    4740
gaacaggcag acatctgtga atcgcttcac gaccacgctg atgagcttta ccgcagctgc    4800
ctcgcgcgtt tcggtgatga cggtgaaaac ctctgacaca tgcagctccc ggagacggtc    4860
acagcttgtc tgtaagcgga tgccgggagc agacaagccc gtcagggcgc gtcagcgggt    4920
gttggcgggt gtcggggcgc agccatgacc cagtcacgta gcgatagcgg agtgtatact    4980
```

```
ggcttaacta tgcggcatca gagcagattg tactgagagt gcaccatata tgcggtgtga      5040
aataccgcac agatgcgtaa ggagaaaata ccgcatcagg cgctcttccg cttcctcgct      5100
cactgactcg ctgcgctcgg tcgttcggct gcggcgagcg gtatcagctc actcaaaggc      5160
ggtaatacgg ttatccacag aatcagggga taacgcagga agaacatgt gagcaaaagg      5220 ccagcaaaag gccaggaacc gtaaaaaggc cgcgttgctg gcgttttcc ataggctccg       5280 cccccctgac gagcatcaca aaaatcgacg ctcaagtcag aggtggcgaa acccgacagg      5340
actataaaga taccaggcgt ttccccctgg aagctccctc gtgcgctctc ctgttccgac      5400
cctgccgctt accggatacc tgtccgcctt tctcccttcg ggaagcgtgg cgctttctca      5460
tagctcacgc tgtaggtatc tcagttcggt gtaggtcgtt cgctccaagc tgggctgtgt      5520
gcacgaaccc cccgttcagc ccgaccgctg cgccttatcc ggtaactatc gtcttgagtc      5580
caacccggta agacacgact tatcgccact ggcagcagcc actggtaaca ggattagcag      5640
agcgaggtat gtaggcggtg ctacagagtt cttgaagtgg tggcctaact acggctacac      5700
tagaaggaca gtatttggta tctgcgctct gctgaagcca gttaccttcg gaaaaagagt      5760
tggtagctct tgatccggca aacaaaccac cgctggtagc ggtggttttt tgtttgcaa       5820 gcagcagatt acgcgcagaa aaaaggatc tcaagaagat cctttgatct tttctacggg      5880
gtctgacgct cagtggaacg aaaactcacg ttaagggatt ttggtcatga acaataaaac      5940
tgtctgctta cataaacagt aatacaaggg gtgttatgag ccatattcaa cgggaaacgt      6000
cttgctctag gccgcgatta aattccaaca tggatgctga tttatatggg tataaatggg      6060
ctcgcgataa tgtcgggcaa tcaggtgcga caatctatcg attgtatggg aagcccgatg      6120
cgccagagtt gtttctgaaa catggcaaag gtagcgttgc caatgatgtt acagatgaga      6180
tggtcagact aaactggctg acggaattta tgcctcttcc gaccatcaag cattttatcc      6240
gtactcctga tgatgcatgg ttactcacca ctgcgatccc cgggaaaaca gcattccagg      6300
tattagaaga atatcctgat tcaggtgaaa atattgttga tgcgctggca gtgttcctgc      6360
gccggttgca ttcgattcct gtttgtaatt gtcctttaa cagcgatcgc gtatttcgtc       6420
tcgctcaggc gcaatcacga tgaataacg gtttggttga tgcgagtgat tttgatgacg      6480
agcgtaatgg ctggcctgtt gaacaagtct ggaaagaaat gcataaactt ttgccattct      6540
caccggattc agtcgtcact catggtgatt tctcacttga taaccttatt tttgacgagg      6600
ggaaattaat aggttgtatt gatgttggac gagtcggaat cgcagaccga taccaggatc      6660
ttgccatcct atggaactgc ctcggtgagt tttctccttc attacagaaa cggctttttc      6720
aaaaatatgg tattgataat cctgatatga ataaattgca gtttcatttg atgctcgatg      6780
agttttctta agaattaatt catgagcgga tacatatttg aatgtattta gaaaaataaa      6840 caaataggg ttccgcgcac atttccccga aaagtgccac ctgaaattgt aaacgttaat      6900
attttgttaa aattcgcgtt aaattttgt taaatcagct cattttttaa ccaataggcc      6960
gaaatcggca aaatccctta taaatcaaaa gaatagaccg agatagggtt gagtgttgtt      7020
ccagtttgga acaagagtcc actattaaag aacgtggact ccaacgtcaa agggcgaaaa      7080
accgtctatc agggcgatgg cccactacgt gaaccatcac cctaatcaag ttttttgggg      7140
tcgaggtgcc gtaaagcact aaatcggaac cctaaaggga gccccgatt tagagcttga      7200 cggggaaagc cggcgaacgt ggcgagaaag gaagggaaga aagcgaaagg agcgggcgct      7260
agggcgctgg caagtgtagc ggtcacgctg cgcgtaacca ccacacccgc cgcgcttaat      7320
```
gcgccgctac agggcgcgtc ccattcgcca                                    7350

<210> SEQ ID NO 9
<211> LENGTH: 8366
<212> TYPE: DNA
<213> ORGANISM: Artificial Sequence
<220> FEATURE:
<223> OTHER INFORMATION: plasmid

<400> SEQUENCE: 9
atccggatat agttcctcct ttcagcaaaa aacccctcaa gacccgttta gaggccccaa     60
ggggttatgc tagttattgc tcagcggtgg cagcagccaa ctcagcttcc tttcgggctt   120
tgttagcagc cggatctcag tggtggtggt ggtggtgctc gagtgcggcc gcaagcttgt   180
cgacttatta tttgaaccaa atgtatctct aaatgattga acaaattgat caaatgtttg   240
aagttgtgaa acttgtgttc catttgcagc ttgatttatt aaattttaa atgctgattc    300
aacagaattt ctaaatgcat caccttttc tgaacctggt gattcatatg tagtccagtt    360
tgcttgatct tttgctgcat ttttaaatac ttgtaatgca ttttctaaga atgggttatc   420
tgttcttgaa ttttttccag aatcaaatgt tttatcagaa actgaatttt gaaaatctga   480
tgttggcatt acatatgaca tttgtttttg gaaaaataat gaaggagttg cagttactgt   540
tgattttgaa tcatctttaa agaaagtata tctttctta gaagttacaa gccaatgtac    600
aaatgctcta gtagcagcat catcaacttc atttgctttt ataccaatta aactaggacc   660
ttgtaaataa attgaatttt ttgctgaatt tcattccat tttgttggag catttattac     720
tacaagttca tttttattta atgtatttga tgaagtttgt tcttcagcag ttccacctag   780
taatttaata tattttccc aatcagcttt aactggattt gaatttgaac ttttcacaaa    840
tacaacaaga cttttttgtg ggttttaga attgctactt tcagcaactc caccataaat    900
aatttcactt gaattttgac tagctgcatt ctttaccact gtttggaaat ctgtaaattc    960
ttgagttttt gaactatcac tttgttgcaa taacaataat ttccaattac ttgtatcgtt  1020
tttaatttta tctatagcag cttgaattga tgcatcgttt gttgtgtcta ttgacttaat  1080
atcaaaacgt gattttaaag taacatttga ttttgcaaga ccatttttaa atgaaccaaa  1140
tcctaaaaat atttgatcac ttgtataatt tgttctatat tttcttccaa gaccattaag  1200
tcctaatcca aatgttaaaa atcctgatct attatagtta tttctatcgc ttttatttgt  1260
tgaagcttta aagttgaaac cagaatattg agagaaatta aaattaattg ttccctcaac  1320
tgattcaata tagttgtgag tataaccagc aattgaacca atactcattg caaatttatg  1380
ataaatttgt ttatttgaag taaattgtcc tggaccttgt aataccacac cctgtgttgc  1440
aactgcgctt ctaaatgttt cataaacagt ttttgctgca acattagctg agaaccctgt  1500
tgttgttaaa gaattataat taacagtatt tactccattt tttttagaag ttgcttcaag  1560
agaattagca taccgatatc cagttaatga ataaacacta ttttggaatg ttgatgtagg  1620
gctgtcaata cctaaaacgt gtaaatcatt ttgattatct tgtgtatttt taaataattt  1680
ttgtgctaat tcagcaaatt taattaaatc ttcataatta ttaaaaatct ttttagaaaa  1740
ttgaaagcct tttaataatt cagttgcgtt atcgactgga tcaccccatt gcttttgaat  1800
ttgacttctg tcaggttgac ccttagaatc tatttctgca acaaaatttt ttgtatcaac  1860
atcatctgag aaagttactc cttttgcttt cattgtgtct aatatataag acataacagg  1920
agcattaata gttgaaacca agtactttt cattattggt aatatgtatg tagatgggtt   1980
tttaatgttt tctgttgttg cgtttgaatt aacaaaatcc ttgttaaata atgaaatatc  2040

```
tgtatctaaa tcaggatttc catttgggtc gttaaaactt aataacatat tgctatttgc    2100
aagtattgcc ccaacaggag aataatttaa aattaagtta aaaaaattat cagtatttt     2160
agcttctaaa tattgcgata cttttttgc tccttcccca taacctgaac caacattatt     2220
tacagtaact tctttgaaaa tatttccaag tttcgctttt aattcggcat cattattata    2280
agcattaact aattcattta aagcttttgc ttgtgctccc ccttgtgaaa aagtcatagc    2340
taaaacaatt ttgtcttttt caacttgctg aaaagcgtta aagatgctt ctggatttgc     2400
gcctaataaa gcgtttaatc ttctatcttt gatagatgaa ttgtcagtaa caccgccaat    2460
attattgtta ctttcattta ttgatccatt tgaacttcca catgatgcag aaatagataa    2520
cgctgcaatt gaacctagcg ttcctaaaat aaatttaatt tttgttttat tcatggatcc    2580
tttaccgctg gtcattttt ggtgttcgtc gaggaattct ttcatctctt tcggcggctg     2640
gtaacccgga acaagtgtgc cattgctcag cacaactgcc ggagtaccgc taacgccaag    2700
ctggacgcca agtgcgtaat ggtcggcaat atccacgtcg caactggctg gtgcgacgct    2760
tttacctgcc atcacatcat caaacgcttt gttttatct ttcgcacacc agatagcttt     2820
catttctttc tctgcatcgc tgtccagccc ctggcgcggg aaagcaagat aacgcacggt    2880
gatccccagc gcgttgtagt ctgccatttg ctcatgcagt ttgtggcagt aaccacaggt    2940
aatatcagta aacacggtga tgacgtgttt tccctgcggc gctttataaa cgatcatctc    3000
ttttcaagc gcattcaact gctttaacag catcttattg gtgacattga ccggagccgt     3060
gccactaacg tcatacattg gcccctgaat gatatgttta ccatcatcgg tgatgtacaa    3120
cacgccgctg ttagtcagaa ctgtcttcat gccagctaca ggcgcgggct gaatatcgct    3180
gcttttgatg cccatttgg ctaacgtttg ttgaattgcc gcgtcatcgg tacccagatc     3240
tgggctgtcc atgtgctggc gttcgaattt agcagcagcg gtttctttca tatgtatatc    3300
tccttcttaa agttaaacaa aattattct agagggaat tgttatccgc tcacaattcc      3360
cctatagtga gtcgtattaa tttcgcggga tcgagatcga tctcgatcct ctacgccgga    3420
cgcatcgtgg ccggcatcac cggcgccaca ggtgcggttg ctggcgccta tatcgccgac    3480
atcaccgatg gggaagatcg gctcgccac ttcgggctca tgagcgcttg tttcggcgtg     3540
ggtatggtgg caggccccgt ggccggggga ctgttgggcg ccatctcctt gcatgcacca    3600
ttccttgcgg cggcggtgct caacggcctc aacctactac tgggctgctt cctaatgcag    3660
gagtcgcata agggagagcg tcgagatccc ggacaccatc gaatggcgca aaacctttcg    3720
cggtatggca tgatagcgcc cggaagagag tcaattcagg gtggtgaatg tgaaaccagt    3780
aacgttatac gatgtcgcag agtatgccgg tgtctcttat cagaccgttt cccgcgtggt    3840
gaaccaggcc agccacgttt ctgcgaaaac gcgggaaaaa gtggaagcgg cgatggcgga    3900
gctgaattac attcccaacc gcgtggcaca acaactggcg gcaaacagt cgttgctgat     3960
tggcgttgcc acctccagtc tggccctgca cgcgccgtcg caaattgtcg cggcgattaa    4020
atctcgcgcc gatcaactgg gtgccagcgt ggtggtgtcg atggtagaac gaagcggcgt    4080
cgaagcctgt aaagcggcgg tgcacaatct tctcgcgcaa cgcgtcagtg ggctgatcat    4140
taactatccg ctggatgacc aggatgccat tgctgtggaa gctgcctgca ctaatgttcc    4200
ggcgttattt cttgatgtct ctgaccagac acccatcaac agtattattt tctcccatga    4260
agacggtacg cgactgggcg tggagcatct ggtcgcattg ggtcaccagc aaatcgcgct    4320
gttagcgggc ccattaagtt ctgtctcggc gcgtctgcgt ctggctggct ggcataaata    4380
```

```
tctcactcgc aatcaaattc agccgatagc ggaacgggaa ggcgactgga gtgccatgtc    4440
cggttttcaa caaaccatgc aaatgctgaa tgagggcatc gttcccactg cgatgctggt    4500
tgccaacgat cagatggcgc tgggcgcaat gcgcgccatt accgagtccg ggctgcgcgt    4560
tggtgcggac atctcggtag tgggatacga cgataccgaa gacagctcat gttatatccc    4620
gccgttaacc accatcaaac aggattttcg cctgctgggg caaaccagcg tggaccgctt    4680
gctgcaactc tctcagggcc aggcggtgaa gggcaatcag ctgttgcccg tctcactggt    4740
gaaaagaaaa accaccctgg cgcccaatac gcaaaccgcc tctccccgcg cgttggccga    4800
ttcattaatg cagctggcac gacaggtttc ccgactggaa agcgggcagt gagcgcaacg    4860
caattaatgt aagttagctc actcattagg caccgggatc tcgaccgatg cccttgagag    4920
ccttcaaccc agtcagctcc ttccggtggg cgcggggcat gactatcgtc gccgcactta    4980
tgactgtctt ctttatcatg caactcgtag gacaggtgcc ggcagcgctc tgggtcattt    5040
tcggcgagga ccgctttcgc tggagcgcga cgatgatcgg cctgtcgctt gcggtattcg    5100
gaatcttgca cgccctcgct caagccttcg tcactggtcc cgccaccaaa cgtttcggcg    5160
agaagcaggc cattatcgcc ggcatggcgg ccccacgggt gcgcatgatc gtgctcctgt    5220
cgttgaggac ccgctaggc tggcggggtt gccttactgg ttagcagaat gaatcaccga    5280
tacgcgagcg aacgtgaagc gactgctgct gcaaaacgtc tgcgacctga gcaacaacat    5340
gaatggtctt cggtttccgt gtttcgtaaa gtctggaaac gcggaagtca gcgccctgca    5400
ccattatgtt ccggatctgc atcgcaggat gctgctggct accctgtgga cacctacat     5460 ctgtattaac gaagcgctgg cattgaccct gagtgatttt tctctggtcc cgccgcatcc    5520
ataccgccag ttgtttaccc tcacaacgtt ccagtaaccg ggcatgttca tcatcagtaa    5580
cccgtatcgt gagcatcctc tctcgtttca tcggtatcat taccccatg aacagaaatc     5640 cccttacac ggaggcatca gtgaccaaac aggaaaaaac cgcccttaac atggcccgct     5700
ttatcagaag ccagacatta acgcttctgg agaaactcaa cgagctggac gcggatgaac    5760
aggcagacat ctgtgaatcg cttcacgacc acgctgatga gctttaccgc agctgcctcg    5820
cgcgtttcgg tgatgacggt gaaaacctct gacacatgca gctcccggag acggtcacag    5880
cttgtctgta agcggatgcc gggagcagac aagcccgtca gggcgcgtca gcgggtgttg    5940
gcgggtgtcg gggcgcagcc atgacccagt cacgtagcga tagcggagtg tatactggct    6000
taactatgcg gcatcagagc agattgtact gagagtgcac catatatgcg gtgtgaaata    6060
ccgcacagat gcgtaaggag aaaataccgc atcaggcgct cttccgcttc ctcgctcact    6120
gactcgctgc gctcggtcgt tcggctgcgg cgagcggtat cagctcactc aaaggcggta    6180
atacggttat ccacagaatc aggggataac gcaggaaaga acatgtgagc aaaaggccag    6240
caaaaggcca ggaaccgtaa aaaggccgcg ttgctggcgt ttttccatag gctccgcccc    6300
cctgacgagc atcacaaaaa tcgacgctca agtcagaggt ggcgaaaccc gacaggacta    6360
taaagatacc aggcgtttcc ccctggaagc tccctcgtgc gctctcctgt tccgaccctg    6420
ccgcttaccg gatacctgtc cgcctttctc ccttcgggaa gcgtggcgct ttctcatagc    6480
tcacgctgta ggtatctcag ttcggtgtag gtcgttcgct ccaagctggg ctgtgtgcac    6540 gaacccccg ttcagcccga ccgctgcgcc ttatccggta actatcgtct tgagtccaac     6600
ccggtaagac acgacttatc gccactggca gcagccactg gtaacaggat tagcagagcg    6660
aggtatgtag gcggtgctac agagttcttg aagtggtggc ctaactacgg ctacactaga    6720
aggacagtat ttggtatctg cgctctgctg aagccagtta ccttcggaaa aagagttggt    6780
```

```
agctcttgat ccggcaaaca aaccaccgct ggtagcggtg gttttttttgt ttgcaagcag    6840 cagattacgc gcagaaaaaa aggatctcaa gaagatcctt tgatcttttc tacggggtct    6900
gacgctcagt ggaacgaaaa ctcacgttaa gggattttgg tcatgaacaa taaaactgtc    6960
tgcttacata acagtaata caaggggtgt tatgagccat attcaacggg aaacgtcttg     7020
ctctaggccg cgattaaatt ccaacatgga tgctgattta tatgggtata aatgggctcg    7080
cgataatgtc gggcaatcag gtgcgacaat ctatcgattg tatgggaagc ccgatgcgcc    7140
agagttgttt ctgaaacatg gcaaaggtag cgttgccaat gatgttacag atgagatggt    7200
cagactaaac tggctgacgg aatttatgcc tcttccgacc atcaagcatt ttatccgtac    7260
tcctgatgat gcatggttac tcaccactgc gatccccggg aaaacagcat tccaggtatt    7320
agaagaatat cctgattcag gtgaaaatat tgttgatgcg ctggcagtgt tcctgcgccg    7380
gttgcattcg attcctgttt gtaattgtcc ttttaacagc gatcgcgtat tcgtctcgc    7440 tcaggcgcaa tcacgaatga taacggtttt ggttgatgcg agtgattttg atgacgagcg    7500
taatggctgg cctgttgaac aagtctggaa agaaatgcat aaacttttgc cattctcacc    7560
ggattcagtc gtcactcatg gtgatttctc acttgataac cttattttg acgagggggaa    7620 attaataggt tgtattgatg ttggacgagt cggaatcgca gaccgatacc aggatcttgc    7680
catcctatgg aactgcctcg gtgagttttc tccttcatta cagaaacggc ttttcaaaa    7740 atatggtatt gataatcctg atatgaataa attgcagttt catttgatgc tcgatgagtt    7800
tttctaagaa ttaattcatg agcggataca tatttgaatg tatttagaaa aataaacaaa    7860 tagggggttcc gcgcacattt ccccgaaaag tgccacctga aattgtaaac gttaatattt    7920
tgttaaaatt cgcgttaaat ttttgttaaa tcagctcatt ttttaaccaa taggccgaaa    7980
tcggcaaaat cccttataaa tcaaaagaat agaccgagat agggttgagt gttgttccag    8040
tttggaacaa gagtccacta ttaaagaacg tggactccaa cgtcaaaggg cgaaaaaccg    8100
tctatcaggg cgatggccca ctacgtgaac catcacccta atcaagtttt tggggtcga    8160 ggtgccgtaa agcactaaat cggaacccta aggggagccc ccgatttaga gcttgacggg    8220
gaaagccggc gaacgtggcg agaaaggaag ggaagaaagc gaaaggagcg ggcgctaggg    8280
cgctggcaag tgtagcggtc acgctgcgcg taaccaccac acccgccgcg cttaatgcgc    8340
cgctacaggg cgcgtcccat tcgcca                                        8366

<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10
gatataggat ccatggcaaa attagatttt gaccgtt                              37

<210> SEQ ID NO 11
<211> LENGTH: 38
<212> TYPE: DNA
<213> ORGANISM: Artificial Sequence
<220> FEATURE:
<223> OTHER INFORMATION: primer

<400> SEQUENCE: 11
caatatgtcg actttaacga ttttttgtaac tgatccgg                            38
```

<210> SEQ ID NO 12
<211> LENGTH: 42
<212> TYPE: DNA
<213> ORGANISM: Artificial Sequence
<220> FEATURE:
<223> OTHER INFORMATION: primer

<400> SEQUENCE: 12
gatataggat ccatggaaaa caaaaaaatt atagttgttg gt            42

<210> SEQ ID NO 13
<211> LENGTH: 43
<212> TYPE: DNA
<213> ORGANISM: Artificial Sequence
<220> FEATURE:
<223> OTHER INFORMATION: primer

<400> SEQUENCE: 13
caatatgtcg acagctttat attttaaacc aagtgctctt aaa            43

<210> SEQ ID NO 14
<211> LENGTH: 46
<212> TYPE: DNA
<213> ORGANISM: Artificial Sequence
<220> FEATURE:
<223> OTHER INFORMATION: primer

<400> SEQUENCE: 14
gatataggat ccatgaataa aacaaaaatt aaatttattt taggaa         46

<210> SEQ ID NO 15
<211> LENGTH: 45
<212> TYPE: DNA
<213> ORGANISM: Artificial Sequence
<220> FEATURE:
<223> OTHER INFORMATION: primer

<400> SEQUENCE: 15
caatatgtcg acattattat ttgaaccaaa tgtatctcta aatga          45

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
gatataggat ccatggaaaa caaaaaaatt atagttgttg gt            42

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
ctttaaacat tcctccaacc caaacagcaa taccacatc                39

<210> SEQ ID NO 18
<211> LENGTH: 39
<212> TYPE: DNA
<213> ORGANISM: Artificial Sequence
<220> FEATURE:
<223> OTHER INFORMATION: primer -continued

```
<400> SEQUENCE: 18
gatgtggtat tgctgtttgg gttggaggaa tgtttaaag                              39

<210> SEQ ID NO 19
<211> LENGTH: 29
<212> TYPE: DNA
<213> ORGANISM: Artificial Sequence
<220> FEATURE:
<223> OTHER INFORMATION: primer

<400> SEQUENCE: 19
ggaggaacta taggccatgt tcctccagc                                         29

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
gctggaggaa catggcctat agttcctcc                                         29

<210> SEQ ID NO 21
<211> LENGTH: 33
<212> TYPE: DNA
<213> ORGANISM: Artificial Sequence
<220> FEATURE:
<223> OTHER INFORMATION: primer

<400> SEQUENCE: 21
catgagaatc ttgtccccaa gaaccaactt gag                                    33

<210> SEQ ID NO 22
<211> LENGTH: 33
<212> TYPE: DNA
<213> ORGANISM: Artificial Sequence
<220> FEATURE:
<223> OTHER INFORMATION: primer

<400> SEQUENCE: 22
ctcaagttgg ttcttgggga caagattctc atg                                    33

<210> SEQ ID NO 23
<211> LENGTH: 43
<212> TYPE: DNA
<213> ORGANISM: Artificial Sequence
<220> FEATURE:
<223> OTHER INFORMATION: primer

<400> SEQUENCE: 23
caatatgtcg acagctttat attttaaacc aagtgctctt aaa                         43

<210> SEQ ID NO 24
<211> LENGTH: 46
<212> TYPE: DNA
<213> ORGANISM: Artificial Sequence
<220> FEATURE:
<223> OTHER INFORMATION: primer

<400> SEQUENCE: 24
gatataggat ccatgaataa aacaaaaatt aaatttattt taggaa                      46

<210> SEQ ID NO 25
```

```
<211> LENGTH: 38
<212> TYPE: DNA
<213> ORGANISM: Artificial Sequence
<220> FEATURE:
<223> OTHER INFORMATION: primer

<400> SEQUENCE: 25
gttatcgact ggatcacccc attgcttttg aatttgac                              38

<210> SEQ ID NO 26
<211> LENGTH: 38
<212> TYPE: DNA
<213> ORGANISM: Artificial Sequence
<220> FEATURE:
<223> OTHER INFORMATION: primer

<400> SEQUENCE: 26
gtcaaattca aaagcaatgg ggtgatccag tcgataac                              38

<210> SEQ ID NO 27
<211> LENGTH: 59
<212> TYPE: DNA
<213> ORGANISM: Artificial Sequence
<220> FEATURE:
<223> OTHER INFORMATION: primer

<400> SEQUENCE: 27
ctatcacttt gttgcaataa caataatttc caattacttg tatcgttttt aattttatc       59

<210> SEQ ID NO 28
<211> LENGTH: 59
<212> TYPE: DNA
<213> ORGANISM: Artificial Sequence
<220> FEATURE:
<223> OTHER INFORMATION: primer

<400> SEQUENCE: 28
gataaaatta aaaacgatac aagtaattgg aaattattgt tattgcaaca aagtgatag       59

<210> SEQ ID NO 29
<211> LENGTH: 45
<212> TYPE: DNA
<213> ORGANISM: Artificial Sequence
<220> FEATURE:
<223> OTHER INFORMATION: primer

<400> SEQUENCE: 29
ctagtaattt aatatatttt tcccaatcag ctttaactgg atttg                      45

<210> SEQ ID NO 30
<211> LENGTH: 45
<212> TYPE: DNA
<213> ORGANISM: Artificial Sequence
<220> FEATURE:
<223> OTHER INFORMATION: primer

<400> SEQUENCE: 30
caaatccagt taaagctgat tgggaaaaat atattaaatt actag                      45

<210> SEQ ID NO 31
<211> LENGTH: 47
<212> TYPE: DNA
<213> ORGANISM: Artificial Sequence
<220> FEATURE:
<223> OTHER INFORMATION: primer

<400> SEQUENCE: 31
```
gaattttttg ctgaattttc attccatttt gttggagcat ttattac                47

<210> SEQ ID NO 32
<211> LENGTH: 47
<212> TYPE: DNA
<213> ORGANISM: Artificial Sequence
<220> FEATURE:
<223> OTHER INFORMATION: primer

<400> SEQUENCE: 32
gtaataaatg ctccaacaaa atggaatgaa aattcagcaa aaaattc                47

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
ctttcttaga agttacaagc caatgtacaa atgctctag                         39

<210> SEQ ID NO 34
<211> LENGTH: 39
<212> TYPE: DNA
<213> ORGANISM: Artificial Sequence
<220> FEATURE:
<223> OTHER INFORMATION: primer

<400> SEQUENCE: 34
ctagagcatt tgtacattgg cttgtaactt ctaagaaag                         39

<210> SEQ ID NO 35
<211> LENGTH: 39
<212> TYPE: DNA
<213> ORGANISM: Artificial Sequence
<220> FEATURE:
<223> OTHER INFORMATION: primer

<400> SEQUENCE: 35
ctggtgattc atatgtagtc cagtttgctt gatcttttg                         39

<210> SEQ ID NO 36
<211> LENGTH: 39
<212> TYPE: DNA
<213> ORGANISM: Artificial Sequence
<220> FEATURE:
<223> OTHER INFORMATION: primer

<400> SEQUENCE: 36
caaaagatca agcaaactgg actacatatg aatcaccag                         39

<210> SEQ ID NO 37
<211> LENGTH: 45
<212> TYPE: DNA
<213> ORGANISM: Artificial Sequence
<220> FEATURE:
<223> OTHER INFORMATION: primer

<400> SEQUENCE: 37
caatatgtcg acattattat ttgaaccaaa tgtatctcta aatga                  45